United States Patent
Schally et al.

(10) Patent No.: US 8,227,421 B2
(45) Date of Patent: *Jul. 24, 2012

(54) FLUORINATED GHRH ANTAGONISTS

(75) Inventors: Andrew Schally, Miami Beach, FL (US); Jozsef Varga, Miami Beach, FL (US); Marta Zarandi, Miami Beach, FL (US); Ren Zhi Cai, Miami, FL (US)

(73) Assignees: University of Miami, Miami, FL (US); The United States of America represented by the Department of Veteran Affairs, Washington, DC (US)

( * ) Notice: Subject to any disclaimer, the term of this patent is extended or adjusted under 35 U.S.C. 154(b) by 300 days.

This patent is subject to a terminal disclaimer.

(21) Appl. No.: 12/562,010

(22) Filed: Sep. 17, 2009

(65) Prior Publication Data
US 2011/0066230 A1    Mar. 17, 2011

(51) Int. Cl.
*A61K 38/16* (2006.01)
*C07K 14/65* (2006.01)
*A61F 2/00* (2006.01)

(52) U.S. Cl. .......... 514/21.3; 514/8.5; 623/1.11
(58) Field of Classification Search .............. None
See application file for complete search history.

(56) References Cited

U.S. PATENT DOCUMENTS
7,452,865 B2 * 11/2008 Schally et al. .............. 514/1.1

OTHER PUBLICATIONS

[Retrieved from website]: http://www.news-medical.net/health/Restenosis-Treatment.aspx, 2 pages [Retrived on Dec. 16, 2011].*

* cited by examiner

*Primary Examiner* — Cecilia J Tsang
*Assistant Examiner* — Satyanarayana R Gudibande

(57) ABSTRACT

Novel fluorinated synthetic analogs of hGH-RH(1-30)NH$_2$ that inhibit the release of growth hormone from the pituitary in mammals as well as inhibit the proliferation of human cancers through a direct effect on the cancer cells, and to therapeutic compositions containing these novel peptides and their use.

19 Claims, 1 Drawing Sheet

FIGURE I
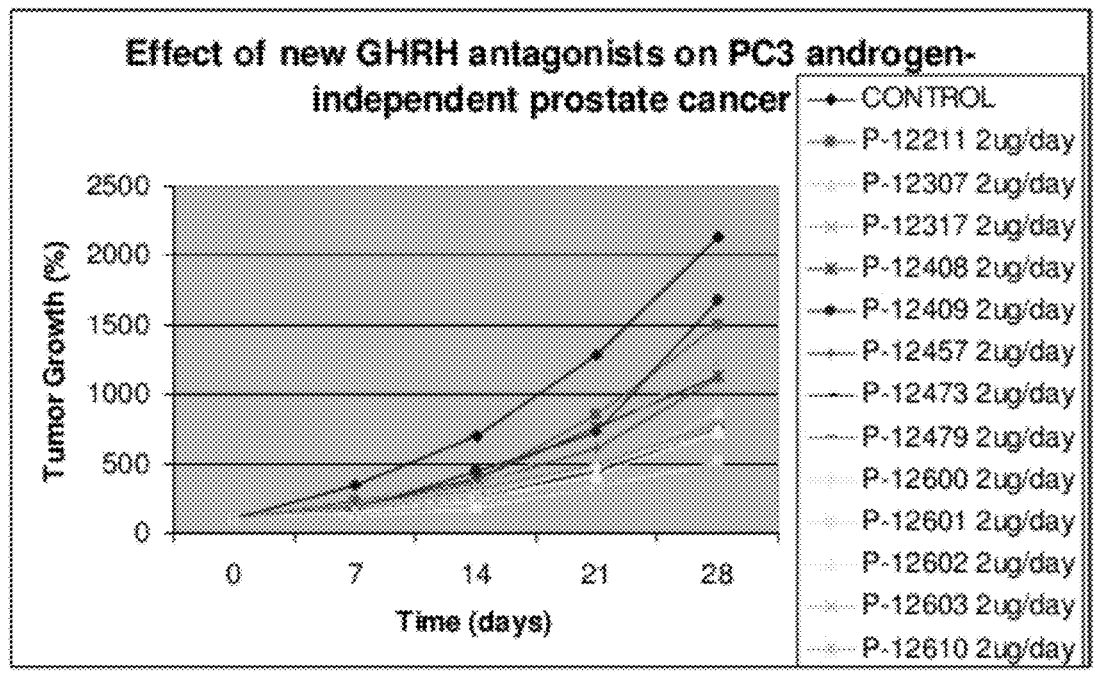
Figure II
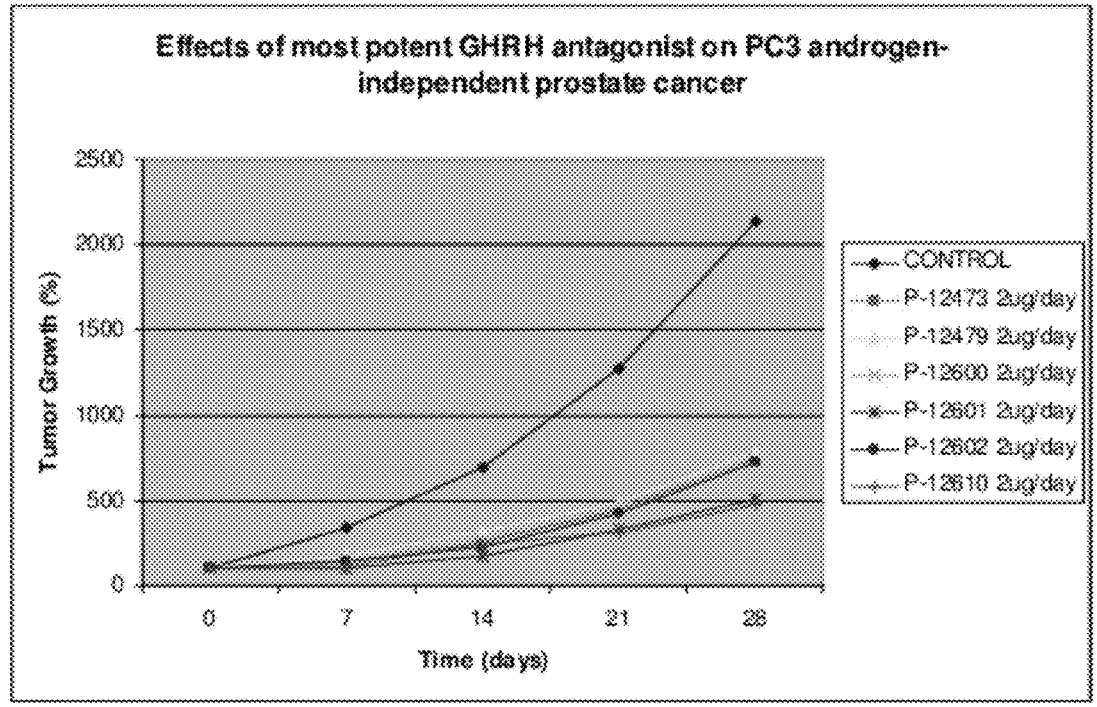

SEQUENCE LISTING

<160> NUMBER OF SEQ ID NOS: 1

<210> SEQ ID NO 1
<211> LENGTH: 29
<212> TYPE: PRT
<213> ORGANISM: Homo sapiens

<400> SEQUENCE: 1

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25
```

FLUORINATED GHRH ANTAGONISTS

This invention was made in part with Government support from the Medical Research Service of the Veterans Affairs Department. The Government has certain rights in this application.

SEQUENCE LISTING

The instant application contains a Sequence Listing which has been submitted via EFS-Web and is hereby incorporated by reference in its entirety. Said ASCII copy, created on Nov. 17, 2009, is named SHAL3036.txt, and is 697 bytes in size.

FIELD OF INVENTION

The present invention relates to novel fluorinated synthetic analogs of hGH-RH(1-30)NH$_2$ that inhibit the release of growth hormone from the pituitary in mammals as well as inhibit the proliferation of human cancers through a direct effect on the cancer cells, and to therapeutic compositions containing these novel peptides and their use.

BACKGROUND OF THE INVENTION

Growth hormone-releasing hormone (GH-RH) is a peptide belonging to the secretin/glucagon family of neuroendocrine and gastrointestinal hormones, a family that also includes vasoactive intestinal peptide (VIP), pituitary adenylate cyclase activating peptide (PACAP) and others. Human GH-RH (hGH-RH) peptide is comprised of 44 amino acid residues. The best known site of production of GH-RH is the hypothalamus, but it was found that various peripheral organs also synthesize it. hGH-RH is also produced, sometimes in large quantities, by human malignant tissues (cancers) of diverse origin.

GH-RH exerts various physiological and pathophysiological functions. Hypothalamic GH-RH is an endocrine releasing hormone that, acting through specific GH-RH receptors on the pituitary, regulates the secretion of pituitary growth hormone (GH). The physiological functions of GH-RH in extrapituitary tissues are less clear. However, there is increasing evidence for the role of GH-RH as an autocrine/paracrine growth factor in various cancers. Splice variant (SV) receptors for GH-RH, different from those expressed in the pituitary, have been described in a wide range of human cancers and in some normal peripheral organs. The actions of tumoral autocrine/paracrine GH-RH could be exerted on these receptors. In addition, receptors for VIP and other, as yet unidentified receptors of this family, could all be targets of local GH-RH.

In view of the role of GH-RH as an endocrine regulator of GH release, novel therapeutic strategies, based on the use of agonistic and antagonistic analogs of GH-RH, have been devised for the treatment of various pathological conditions.

GH is a polypeptide having 191 amino acids that stimulates the production of different growth factors, e.g. insulin-like growth factor I (IGF-I), and consequently promotes growth of numerous tissues (skeleton, connective tissue, muscle and viscera) and stimulates various physiological activities (raising the synthesis of nucleic acids and proteins, and raising lipolysis, but lowering urea secretion). Release of pituitary GH is under the control of releasing and inhibiting factors secreted by the hypothalamus, the primary releasing factors being GH-RH and ghrelin, and the main inhibiting factor being somatostatin.

GH has been implicated in several diseases. One disease in which GH is involved is acromegaly, in which excessive levels of GH are present. The abnormally enlarged facial and extremity bones, and the cardiovascular symptoms of this disease can be treated by administering a GH-RH antagonist. Further diseases involving GH are diabetic retinopathy and diabetic nephropathy. The damage to the retina and kidneys respectively in these diseases, believed to be due to hypersecretion of GH, results in blindness or reduction in kidney function. This damage can be prevented or slowed by administration of an effective GH-RH antagonist.

In an effort to intervene in these disease and other conditions, some investigators have attempted to control GH and IGF-I levels by using analogs of somatostatin, an inhibitor of GH release. However, somatostatin analogs, if administered alone, do not suppress GH or IGF-I levels to a desired degree. If administered in combination with a GH-RH antagonist, somatostatin analogs will suppress IGF-I levels much better.

However, the main applications of GH-RH antagonists are in the field of cancer (reviewed in Schally A V and Varga J L, Trends Endocrinol Metab 10: 383-391, 1999; Schally A V et al, Frontiers Neuroendocrinol 22: 248-291, 2001; Schally A V and Comaru-Schally A M, in: Kufe D W, Pollock R E, Weichselbaum R R, Bast Jr. R C, Gansler T S, Holland J F, Frei III E, Eds. Cancer Medicine, 6$^{th}$ ed. Hamilton, Ontario: BC. Decker, Inc., 2003, p. 911-926). GH-RH antagonists inhibit the proliferation of malignancies by indirect endocrine mechanisms based on the inhibition of pituitary GH release and resulting in the decrease of serum levels of GH and IGF-I, as well as by direct effects on the tumor tissue.

GH-RH and its tumoral splice variant (SV) receptors are present in human cancers of the lung, prostate, breast, ovary, endometrium, stomach, intestine, pancreas, kidney, and bone (see Halmos G et al, Proc Natl Acad Sci USA 97: 10555-10560, 2000; Rekasi Z et al, Proc Natl Acad Sci USA 97: 10561-10566, 2000; Schally A V et al, Frontiers Neuroendocrinol 22: 248-291, 2001; Schally A V and Comaru-Schally A M, in: Kufe D W, Pollock R E, Weichselbaum R R, Bast Jr. R C, Gansler T S, Holland J F, Frei III E, Eds. Cancer Medicine, 6$^{th}$ ed. Hamilton, Ontario: BC. Decker, Inc., 2003, p. 911-926). Tumoral GH-RH has been shown or it is suspected to act as an autocrine growth factor in these malignancies. Antagonistic analogs of GH-RH can inhibit the stimulatory activity of GH-RH and exert direct antiproliferative effects in vitro on cancer cells, and in vivo on tumors. Direct antiproliferative effects of GH-RH antagonists are exerted on tumoral receptors (binding sites). In addition to the specific tumoral SV receptors for GH-RH, receptors for VIP and other, as yet unidentified receptors of this family, are targets of GH-RH antagonists.

In addition to endocrine inhibitory effects on serum GH and IGF-I, GH-RH antagonists have been found to reduce the autocrine and paracrine production of several tumor growth factors and/or downregulate their receptors. These growth factors include IGF-I, IGF-II, GH, vascular endothelial growth factor (VEGF), and fibroblast growth factor (FGF), Thus, a disruption of the autocrine/paracrine stimulatory loops based on these growth factors contributes to the efficacy of GH-RH antagonists as antitumor agents.

IGF-I and IGF-II are autocrine/paracrine growth factors with potent mitogenic effects on various cancers. IGF-I is also an endocrine growth factor, and elevated levels of serum IGF-I are considered an epidemiological risk factor for the development of prostate cancer, lung cancer, and colorectal cancer. The involvement of IGF-I (somatomedin-C) in breast cancer, prostate cancer, colon cancer, bone tumors and other malignancies is well established. Nevertheless, autocrine/ paracrine control of proliferation by IGF-II is also a major factor in many tumors. IGF-I and IGF-II exert their proliferative and anti-apoptotic effects through the common IGF-I receptor. The receptors for IGF-I are present in primary human breast cancers, prostate cancers, lung cancers, colon cancers, brain tumors, pancreatic cancers, and in renal cell carcinomas. In several experimental cancers, such as those of the bone, lung, prostate, kidney, breast, ovary, intestine, pancreas, and brain, treatment with GH-RH antagonists produces a reduction in IGF-I and/or IGF-II levels, concomitant to inhibition of tumor growth (reviewed in Schally A V and Varga J L, Trends Endocrinol Metab 10: 383-391, 1999; Schally A V et al, Frontiers Neuroendocrinol 22: 248-291, 2001; Schally A V and Comaru-Schally A M, in: Kufe D W, Pollock R E, Weichselbaum R R, Bast Jr. R C, Gansler T S, Holland J F, Frei III E, Eds. Cancer Medicine, $6^{th}$ ed. Hamilton, Ontario: BC. Decker, Inc., 2003, p. 911-926). In some cases, the expression of IGF-I receptors was also decreased by GH-RH antagonists. Thus the disruption of endocrine and autocrine/paracrine stimulatory loops dependent on IGF-I and IGF-II contributes to the antitumor effect of GH-RH antagonists.

In MXT breast cancer model, treatment with GH-RH antagonists inhibited tumor growth, reduced the mRNA level for GH and the concentration of GH peptide in tumors, and inhibited the mRNA expression for GH receptors (Szepeshazi K et al, Endocrinology 142: 4371-4378, 2001). GH was shown to act as a growth factor for MXT murine mammary carcinoma cells, MCF-7 human breast cancer cells and other tumor cell lines. Thus the inhibitory activity of GH-RH antagonists on local and serum GH levels contributes to their antitumor effect.

GH-RH antagonists have been shown to inhibit the mRNA levels and protein concentrations of VEGF in human androgen-sensitive and androgen-independent prostate cancer models (Letsch M et al, Proc Natl Acad Sci USA 100: 1250-1255, 2003; Plonowski A et al, Prostate 52: 173-182, 2002) and this phenomenon contributes to their antitumor effect, since VEGF plays an important stimulatory role in the neovascularization and growth of various tumors. Moreover, it was found that a GH-RH antagonist inhibited the VEGF secretion and proliferation of normal murine endothelial cells, apparently through a direct effect on these cells in vitro (Siejka A et al, Life Sci 72: 2473-2479, 2003).

Scientists have investigated various modifications of GH-RH to elucidate the relationship of the structure of GH-RH to its activity on the pituitary receptors, in an effort to provide synthetic congeners with improved agonistic or antagonistic properties. Thus, it was early established that GH-RH fragment comprising residues 1 to 29, or GH-RH(1-29), is the minimum sequence necessary for biological activity on the pituitary. This fragment retains 50% or more of the potency of native GH-RH. Subsequently, many synthetic analogs of GH-RH, based on the structure of hGH-RH(1-29)$NH_2$ peptide, were prepared. hGH-RH(1-29)$NH_2$ has the following amino acid sequence:

Tyr-Ala-Asp-Ala-Ile$^5$-Phe-Thr-Asn-Ser-Tyr$^{10}$-Arg-Lys-Val-Leu-Gly$^{15}$-Gln-Leu-Ser-Ala-Arg$^{20}$-Lys-Leu-Leu-Gln-Asp$^{25}$-Ile-Met-Ser-Arg$^{29}$-$NH_2$ (SEQ ID NO: 1)

A considerable number of patents and articles in the open literature disclose analogs of GH-RH which either act as agonists of GH-RH (i.e. act to stimulate the release of GH) or as antagonists of GH-RH (i.e. act to inhibit the release of GH) on the pituitary. Most of these peptides are derived from the GH-RH(1-29) peptide sequence, with specific structural modifications which account for their enhanced agonistic or antagonistic properties on the pituitary receptors. However, apart from a few exceptions, it is not known how these analogs would behave on cancer cells that express GH-RH receptors different from those found in the pituitary. Only a few published scientific studies tried to elucidate the structure-activity relationships and characterize the direct antagonistic (or agonistic) effects of GH-RH analogs on cancer cells and tumors (see Rekasi Z et al, Endocrinology 141: 2120-2128, 2000; Halmos G et al, Proc Natl Acad Sci USA 97: 10555-10560, 2000; Rekasi Z et al, Proc Natl Acad Sci USA 97: 10561-10566, 2000; Kiaris H et al, Proc Natl Acad Sci USA 99: 196-200, 2002), and no issued patents have dealt with this issue so far. Consequently, very little is known about the structural features in GH-RH analogs required for a direct antagonistic action on tumor cells.

The first described GH-RH antagonist, [Ac-Tyr$^1$,D-Arg$^2$] hGH-RH(1-29)$NH_2$ which is generally termed as the "standard antagonist" in the literature, was found to prevent the activation of rat anterior pituitary adenylate cyclase by hGH-RH(1-29)$NH_2$. The same peptide blocked the action of GH-RH on its receptors in the pituitary and hypothalamus, and inhibited the pulsatile growth hormone secretion. The standard antagonist was also evaluated clinically (Ocampo-Lim B et al, J Clin Endocrinol Metab 81: 4396-4399, 1996; Jaffe C A et al, J Clin Endocrinol Metab 82: 634-637, 1997). Large doses of this antagonist (400 μg/kg) eliminated nocturnal GH secretion in normal subjects and inhibited the response to GH-RH. The standard GH-RH antagonist also reduced GH levels in a patient with acromegaly. However, for clinical use, much more potent antagonists of GH-RH are required.

The inventions mentioned below disclose GH-RH analogs with antagonistic or agonistic properties on the pituitary receptors for GH-RH. However it was not reported and not investigated whether these analogs could exert direct effects on tumor cells.

U.S. Pat. No. 4,659,693 discloses GH-RH antagonistic analogs which contain certain N,N'-dialkyl-omega-guanidino alpha-amino acyl residues in position 2 of the GH-RH (1-29) sequence.

Published application WO 91/16923 reviews earlier attempts to alter the secondary structure of hGH-RH by modifying its amino acid sequence. These earlier attempts include: replacing Tyr$^1$, Ala$^2$, Asp$^3$ or Asn$^8$ with their D-isomers; replacing Asn$^8$ with L- or D-Ser, D-Arg, Asn, Thr, Gln or D-Lys; replacing Ser$^9$ with Ala to enhance amphiphilicity of the region; and replacing Gly$^{15}$ with Ala or Aib. When $R^2$ in the analogs is D-Arg, and $R^8$, $R^9$, and $R^{15}$ are substituted as indicated above, antagonistic activity is said to result. These antagonistic peptides are said to be suitable for administration as pharmaceutical compositions to treat conditions associated with excessive levels of GH, e.g., acromegaly.

The antagonistic activity of the hGH-RH analogue "[Ser$^9$-psi[$CH_2$—NH]-Tyr$^{10}$]hGH-RH(1-29) of U.S. Pat. No. 5,084,555 was said to result from the pseudopeptide bond (i.e., a peptide bond reduced to a [$CH_2$—NH] linkage) between the $R^9$ and $R^{10}$ residues. However, the antagonistic properties of [Ser$^9$-psi[$CH_2$—NH]-Tyr$^{10}$]hGH-RH(1-29) were said to be inferior to the standard antagonist, [Ac-Tyr$^1$, D-Arg$^2$]hGH-RH(1-29)-$NH_2$ U.S. Pat. No. 5,550,212, U.S. Pat. No. 5,942,489, and U.S. Pat. No. 6,057,422, disclose analogs of hGH-RH(1-29)$NH_2$ said to have enhanced antagonistic properties and prolonged duration of action regarding the inhibition of GH-RH-evoked GH release. These properties are believed to result from replacement of various amino acids and acylation with aromatic or nonpolar acids at the N-terminus of GH-RH (1-29)$NH_2$. The tumor inhibitory properties of antagonists featured in U.S. Pat. No. 5,942,489 and U.S. Pat. No. 6,057,422 have been demonstrated by using nude mice bearing xenografts of experimental human cancer models. It is noted that in U.S. Pat. No. 5,550,212, and in U.S. Pat. No. 5,942, 489, $R^9$ is always Ser, while $R^{11}$ and $R^{20}$ can be either Arg, D-Arg, or Cit. In the case of U.S. Pat. No. 6,057,422, $R^9$ can be either Arg, Har, Lys, Orn, D-Arg, D-Har, D-Lys, D-Orn, Cit, Nle, Tyr(Me), Ser, Ala, or Aib, while $R^{11}$ and $R^{20}$ are always Arg.

It is noted that no published prior art discloses the synthesis and use of GHRH analogs with di- or poly-fluorinated phenylalanine substitution in positions 6 and/or 10.

BRIEF DESCRIPTION OF THE DRAWINGS

FIG. I is a plot of tumor growth in % against time for the effect of new GHRH antagonists on PC3 and androgen independent prostate cancer.

FIG. II is a plot of tumor growth in % against time for the effect of the most potent GHRH antagonists androgen independent prostate cancer.

SUMMARY OF THE INVENTION

There is provided a novel series of synthetic analogs of hGH-RH(1-29)$NH_2$ and hGH-RH(1-30)$NH_2$. These analogs inhibit the release of growth hormone from the pituitary in mammals as well as inhibit the proliferation of human cancers through a direct effect on the cancer cells. The stronger inhibitory potencies of the new analogs, as compared to previously described ones, results from replacement of various amino acids.

The invention principally relates a peptide selected from the group having the formulae: [$R_1$-$A^0$, $A^1$, $A^2$, $A^6$, $A^8$, $A^9$, $A^{10}$,$A^{11}$,$A^{12}$,$A^{13}$, $A^{15}$,$A^{17}$,$A^{19}$,$A^{20}$,$A^{21}$,$A^{22}$,$A^{23}$,$A^{27}$,$A^{28}$, $A^{29}$-$A^{30}$]hGH-RH(1-30)-$R_2$
wherein
$R_1$ is a member of the group consisting of
a) phenylacetic acid or phenylpropionic acid mono- or poly-fluorinated on the aromatic ring;
b) H, PhAc, Fpr, 1-Nac, 2-Nac, 1-Npr, 2-Npr, Ibu, Dca, Fer;
c) $CH_3(CH_2)_nCO$, $HOOC(CH_2)_nCO$, where n is an integer from 2 to 24;
and d) any other straight chain, cyclic, branch chain, saturated, unsaturated, or poly unsaturated aliphatic carboxyl group of 6-18 carbon atoms and any 3-8 carbon containing carboxylic acids with aromatic or heterocyclic aromatic ring containing up to one atom each of the group S, N, and O in the heterocyclic ring,
$A^0$ is a member of the group consisting of
a) an Oaa with 4 to 24 carbon atoms, containing either straight or branched, saturated, unsaturated or poly unsaturated aliphatic carbon chain, including, but not limited to ω-Aha, ω-Aoc, and ω-Ada;
b) an Oaa-Oaa dimer linked by an amide bond between the carboxyl group of the first Oaa and the N atom of the second Oaa;
c) an Oaa-Oaa-Oaa trimer; and
d) Phe, D-Phe, Arg, D-Arg, or is absent.
$A^1$ is L-Fpa, D-Fpa, Tyr, D-Tyr, His or D-His,
$A^2$ is D-Arg, D-Har, D-Cit, or D-Amp,
$A^6$ is Fpa, Cpa, Phe, Tyr, Nal, or Phe(Y), in which Y=Cl, Br, or I
$A^8$ is Asn, D-Asn, Cit, D-Cit, Gln, D-Gln, Ser, D-Ser, Thr, D-Thr, Ala, D-Ala, N-Me-Ala, N-Me-D-Ala, Abu, D-Abu, or Aib,
$A^9$ is Har, D-Har, Arg, D-Arg, Fpa, D-Fpa, His, D-His, Amp, D-Amp, Gup, or D-Gup,
$A^{10}$ is di- or poly-fluorinated (on the aromatic ring) Phe: Fpa2, Fpa3, Fpa4, or Fpa5,
$A^{11}$ is His, D-His, Arg, D-Arg, Cit, D-Cit, Har, D-Har, Amp, D-Amp, Gup, or D-Gup,
$A^{12}$ is Lys, D-Lys, Lys(Me)$_2$, Lys(iPr), Orn, D-Orn, Har, D-Har, Cit, D-Cit, Nle, D-Nle, Ala, or D-Ala,
$A^{13}$ is Fpa, Val or Leu,
$A^{15}$ is Fpa, Gly, Ala, Abu, Aib, Nle, Gln, Cit, or His,
$A^{17}$ is Leu or Glu,
$A^{19}$ is Ala or Abu,
$A^{20}$ is His, D-His, Arg, D-Arg, Har, D-Har-, Amp, D-Amp, Cit, or D-Cit,
$A^{21}$ is Lys, D-Lys, Lys(Me)$_2$, Lys(iPr), Orn, D-Orn, Har, D-Har, Cit, or D-Cit,
$A^{22}$ is Fpa, Leu, Tyr, Ala, or Aib,
$A^{23}$ is Fpa, Leu, Tyr, Ala, or Aib,
$A^{27}$ is Nle, Met, Leu, Ala, Abu, α-Apa, α-Ahea, or α-Aoc,
$A^{28}$ is Arg, D-Arg, Har, D-Har, Ser, Asn, Asp, Ala, Abu, or Cit,
$A^{29}$ is Arg, D-Arg, Har, D-Har, Cit, D-Cit, or Agm,
$A^{30}$ is Oaa, Oaa-Oaa dimer, Oaa-Oaa-Oaa trimer, β-Ala, —NH—(CH$_2$—CH$_2$—O—)$_n$—(CH$_2$)$_m$—CO— where n is an integer from 1 to 30, m is an integer from 1 to 18, Arg, D-Arg, Har, D-Har, Cit, D-Cit, Agm, or is absent,
$R_2$ is —$NH_2$, —NH—$NH_2$, —NH—OH, —$NHR_3$, —$NR_3R_4$, —OH, or —$OR_3$, in which $R_3$ and $R_4$ are selected from the group consisting of $C_{1-10}$ alkyl, $C_{2-10}$ alkenyl, $C_{2-10}$ alkinyl, —$C_6H_5$, and mono- or diphenyl $C_{1-18}$alkyl;
provided that if $A^{29}$ is Agm then $A^{30}$ and $R_2$ are absent, and if $A^{30}$ is Agm then $R_2$ is absent,
and pharmaceutically acceptable salts thereof.

Preferred of these peptides are those wherein
$A^0$ is a member of the group consisting of
ω-Aha, ω-Aoc, and ω-Ada.

Particularly preferred of these peptides are those wherein, the substituent in at least one member of the group consisting of $A^1$, $A^6$, $A^{10}$, $A^{13}$, $A^{15}$, or $A^{22}$ is di- or poly-fluorinated Phe. $R_1$ is a phenylacetic acid or phenylpropionic acid being polyfluorinated on the aromatic ring.

Especially preferred among these peptide are those wherein, the substituent in at least one member of the group consisting of $A^1$, $A^6$, or $A^{10}$, is Fpa4 or Fpa5.

The peptides of greatest interest are those selected from the group having the formulae:
$R_1$-$A^0$,$A^1$,D-Arg$^2$,$A^6$,$A^8$,Har$^9$,$A^{10}$,His$^{11}$,Orn$^{12}$,Val$^{13}$,$A^{15}$, $A^{17}$,Ala$^{19}$,His$^{20}$, Orn$^{21}$,Leu$^{22}$,Leu$^{23}$,Har$^{28}$-D-Arg$^{29}$,$A^{30}$] hGH-RH(1-30)-$R_2$
wherein:
$R_1$ is Ac, (Ac-Ada), PhAc and PhF$_5$Ac,
$A^0$ is Dca, PhAc, PhF$_5$Ac, (Dca-Ada), (CH$_3$—(CH$_2$)$_{10}$—CO-Ada), (Ac-Ada), (PhAc-Ada), or (PhF$_5$Ac-Ada),
$A^1$ is Tyr or Fpa5,
$A^6$ is Fpa5,
$A^8$ is (Me-Ala),
$A^{10}$ is Fpa5,
$A^{15}$ is His,
$A^{17}$ is Glu,
$A^{30}$ is Ada or Agm,
$R_2$ is —$NH_2$, —OH, or absent It is noted that the amino acid residues from 30 through 44 of the native GH-RH molecule do not appear to be essential to activity; nor does their identity appear to be critical. Therefore, it appears that the addition of some or all of these further amino acid residues to the C-terminus of the hGH-RH(1-29) $NH_2$ and hGH-RH(1-30)$NH_2$ analogs of the present invention will not affect the efficacy of these analogs as GH-RH antagonists.

If some or all of these amino acids were added to the C-terminus of the hGH-RH(1-29)NH$_2$ analogs, the added amino acid residues could be the same as residues 30 through 44 in the native hGH-RH sequence or reasonable equivalents.

Synthetic Methods.

The synthetic peptides are synthesized by a suitable method such as by exclusive solid phase techniques, by partial solid-phase techniques, by fragment condensation or by classical solution phase synthesis. When the analogs of this invention are synthesized by solid-phase method, the C-terminus residue (here, A$^{29}$ or A$^{30}$) is appropriately linked (anchored) to an inert solid support (resin) while bearing protecting groups for its alpha amino group (and, where appropriate, for its side chain functional group). After completion of this step, the alpha amino protecting group is removed from the anchored amino acid residue and the next amino acid residue, A$^{28}$ or A$^{29}$ respectively, is added having its alpha amino group (as well as any appropriate side chain functional group) suitably protected, and so forth. The N-terminus protecting groups are removed after each residue is added, but the side chain protecting groups are not yet removed. After all the desired amino acids have been linked in the proper sequence, the peptide is cleaved from the support and freed from all side chain protecting group(s) under conditions that are minimally destructive towards residues in that sequence. This is be followed by a careful purification and scrupulous characterization of the synthetic product, so as to ensure that the desired structure is indeed the one obtained.

It is particularly preferred to protect the alpha amino function of the amino acids during the coupling step with an acid or base sensitive protecting group. Such protecting groups should have the properties of being stable in the conditions of peptide linkage formation, while being readily removable without destruction of the growing peptide chain and without racemization of any of the chiral centers contained therein. Suitable alpha amino protecting groups are Boc and Fmoc.

Medical Applications.

The hGH-RH antagonist peptides, or salts of these peptides, may be formulated in pharmaceutical dosage forms containing effective amounts thereof and administered to humans or animals for therapeutic or diagnostic purposes. The peptides may be used to suppress GH levels and to treat conditions associated with excessive levels of GH, e.g., diabetic retinopathy and nephropathy, and acromegaly. Also provided are methods for treating these diseases by administration of a composition of the invention to an individual needing such treatment. The main uses of GH-RH antagonists are, however, in the field of cancer, for example human cancers of the lung, prostate, breast, ovary, endometrium, stomach, colon, pancreas, kidney, bone, and brain where the receptors for GH-RH, IGF-I/IGF-II, or GH are present, and that depend on stimulation by growth factors such as GH-RH, IGF-I, IGF-II, GH, VEGF, or FGF.

DETAILED DESCRIPTION OF THE PREFERRED EMBODIMENTS

The nomenclature used to define the peptides is that specified by the IUPAC-IUB Commission on Biochemical Nomenclature wherein, in accordance with conventional representation, the amino group at the N-terminus appears to the left and the carboxyl group at the C-terminus appears to the right. The term "natural amino acid" as used herein means one of the common, naturally occurring L-amino acids found in naturally occurring proteins: Gly, Ala, Val, Leu, Ile, Ser, Thr, Lys, Arg, Asp, Asn, Glu, Gln, Cys, Met, Phe, Tyr, Pro, Trp and His. When the natural amino acid residue has isomeric forms, it is the L-form of the amino acid that is represented herein unless otherwise expressly indicated.

Non-coded amino acids, or amino acid analogues, are also incorporated into the GH-RH antagonists. ("Non-coded" amino acids are those amino acids which are not among the approximately 20 natural amino acids found in naturally occurring proteins.) When these non-coded amino acids, or amino acid analogues, have isomeric forms, it is the L-form of the amino acid that is represented unless otherwise expressly indicated.

ABBREVIATIONS

Abu alpha-aminobutyric acid
Ac acetyl
AcOH acetic acid
Ac$_2$O acetic anhydride
Ada 12-aminododecanoyl
AE$_2$A 8-amino-3,6-dioxaoctanoyl
AE$_4$P 15-amino-4,7,10,13-tetraoxapentadecanoyl
Agm agmatine
Aha aminohexanoic acid
Ahea aminohexanoic acid
Ahx 6-Aminohexanoyl
Amc 8-Aminocaprylyl
Aoc aminooctanoic acid
Apa 5-Aminopentanoyl
Aib alpha-aminoisobutyroyl
All allyl
Alloc allyloxycarbonyl
Amp para-amidino-phenylalanine
Bpa para-benzoyl-phenylalanine
Boc tert-butyloxycarbonyl
Bom benzyloxymethyl
2BrZ 2-bromo-benzyloxycarbonyl
Bzl benzyl
Cha cyclohexylalanine
Chg cyclohexylglycine
cHx cyclohexyl
Cit citrulline (2-amino-5-ureidovaleroyl
2ClZ 2-chloro-benzyloxycarbonyl
Cpa para-chlorophenylalanine
Dat des-amino-tyrosine
Dca Dichloroacetyl
DCM dichloromethane
DIC N,N'-diisopropylcarbodiimide
DIEA diisopropylethylamine
Dip (3,3-diphenyl)alanine
DMF dimethylformamide
Et ethyl
Fer ferulyl
FGF fibroblast growth factor
Fm fluorenylmethyl
Fmoc fluorenylmethoxycarbonyl
For formyl
Fpa mono- or poly-fluorinated Phe (fluorine substitution on the aromatic ring)
Fpa2 difluoro-Phe
Fpa3 trifluoro-Phe
Fpa4 tetrafluoro-Phe
Fpa5 pentafluoro-Phe
Fpr fluoropropionyl
GH growth hormone
GH-RH GH releasing hormone
Gup para-guanidino-phenylalanine
Har homoarginine HBTU 2-(1H-Benzotriazol-1-yl)-1,1,3,3-tetramethyluronium hexafluorophosphate
Hca hydrocinnamoyl
Hca-OH hydrocinnamic acid
hGH-RH human GH-RH
HMBA 4-hydroxymethyl benzoyl
HOBt 1-hydroxybenzotriazole
HPLC high performance liquid chromatography
Ibu isobutyryl
IndAc indole-3-acetyl
Ipa indole-3-propionyl
Lys(0-11) Lys($A^0$-$A^1$-$A^2$-$A^3$-$A^4$-$A^5$-$A^6$-$A^7$-$A^8$-$A^9$-$A^{10}$-$A^{11}$-)
ε-Lys(α-$NH_2$) a Lys residue, the ε-amino group of which is acylated by the carbonyl group of an N-terminally located amino acid; the α-amino group of the Lys residue is free
MBHA para-methylbenzhydrylamine
Me methyl
Me-Ala N-methyl-Ala
MeOH methanol
MeCN acetonitrile
Nac naphthylacetyl
Nal naphthylalanine
Nle norleucine
NMM N-methylmorpholine
Npr naphthylpropionyl
Oaa omega-amino acid
Oct octanoyl
Orn ornithine
Peg pegyl
Pal pyridylalanine
PAM phenylacetamidomethyl
Ph phenyl
PhAc phenylacetyl
PhAc-OH phenylacetic acid
Phe(pCl) para-chloro-phenylalanine
Phe(p$NH_2$) para-amino-phenylalanine
Phe(p$NO_2$) para-nitro-phenylalanine
PhPr phenylpropionyl
rGH-RH rat GH-RH
RP-HPLC reversed phase HPLC
Sub suberyl
SPA para-sulfonyl-phenoxyacetyl
TFA trifluoroacetic acid
Tos para-toluenesulfonyl
Tpi 1,2,3,4-tetrahydronorharman-3-carboxylic acid
Tyr(Me) O-methyl-tyrosine
Tyr(Et) O-ethyl-tyrosine
Z benzyloxycarbonyl B. The GH-RH Analogs The hGH-RH analogs of the present invention were designed to increase the antagonistic effects at the pituitary level, and/or at the tumoral level. Particularly preferred are the peptides of the structure shown in Table A below:

TABLE A

| | |
|---|---|
| P-12610 | [PhAc$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$, Ada$^{30}$]hGH-RH(1-30)$NH_2$ |
| P-12640 | [PhAc$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12642 | [PhAc$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12644 | [PhAc$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12646 | [(PhAc-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)$NH_2$ |
| P-12650 | [(PhF$_5$Ac)$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$,]hGH-RH(1-29)$NH_2$ |
| P-12652 | [(PhF$_5$Ac)$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12656 | [(PhF$_5$Ac)$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12660 | [PhAc$^0$-Tyr$^1$, D-Arg$^2$, Cpa$^6$, Ala$^8$, Har$^9$, Fpa5$^{10}$, His$^{11}$, Orn$^{12}$, His$^{15}$, His$^{20}$, Orn$^{21}$, Nle$^{27}$, D-Arg$^{28}$, Har$^{29}$, Ada$^{30}$]hGH-RH(1-30)$NH_2$ |
| P-12662 | [PhAc$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12664 | [(PhF$_5$Ac)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12666 | [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12670 | [PhAc$^0$-Tyr$^1$, D-Arg$^2$, Fpa5$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12672 | [(PhF$_5$Ac)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12674 | [(PhF$_5$Ac)$^0$-Tyr$^1$,, D-Arg$^2$, Fpa5$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)$NH_2$ |
| P-12680 | [(Ac-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)$NH_2$ |
| P-12682 | [(Ac-Ada)$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)$NH_2$ |
| P-12684 | [(Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$,]hGH-RH(1-29)$NH_2$ |
| P- | [(PhAc-Ada)$^0$-Tyr$^1$, D-Arg$^2$, Cpa$^6$, Ala$^8$, Har$^9$, Fpa5$^{10}$, His$^{11}$, Orn$^{12}$, |

TABLE A-continued

| | |
|---|---|
| 12690 | Abu¹⁵, His²⁰, Orn²¹, Nle²⁷, D-Arg²⁸, Har²⁹]hGH-RH(1-29)NH₂ |
| P-12692 | [(PhF₅Ac-Ada)⁰-Tyr¹, D-Arg², Cpa⁶, Ala⁸, Har⁹, Fpa5¹⁰, His¹¹, Orn¹², Abu¹⁵, Glu¹⁷, His²⁰, Orn²¹, Nle²⁷, D-Arg²⁸, Har²⁹]hGH-RH(1-29)NH₂ |
| P-12694 | [(PhAc-Ada)⁰-Tyr¹, D-Arg², Cpa⁶, (Me-Ala)⁸, Har⁹, Fpa5¹⁰, His¹¹, Orn¹², Abu¹⁵, His²⁰, Orn²¹, Nle²⁷, D-Arg²⁸, Har²⁹]hGH-RH(1-29)NH₂ |
| P-12696 | [(PhAc-Ada)⁰-Tyr¹, D-Arg², Cpa⁶, (Me-Ala)⁸, Har⁹, Fpa5¹⁰, His¹¹, Orn¹², His¹⁵, His²⁰, Orn²¹, Nle²⁷, D-Arg²⁸, Har²⁹]hGH-RH(1-29)NH₂ |
| P-12698 | [(PhAc-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹]hGH-RH(1-29)NH₂ |
| P-12710 | [(PhAc-Ada)⁰-Tyr¹, D-Arg², Cpa⁶, Ala⁸, Har⁹, Fpa5¹⁰, His¹¹, Orn¹², His¹⁵, Glu¹⁷, His²⁰, Orn²¹, Nle²⁷, D-Arg²⁸, Har²⁹]hGH-RH(1-29)NH₂ |
| P-12712 | [(PhAc-Ada)⁰-Tyr¹, D-Arg², Cpa⁶, Ala⁸, Har⁹, Fpa5¹⁰, His¹¹, Orn¹², Leu¹³, Abu¹⁵, Glu¹⁷, His²⁰, Orn²¹, Nle²⁷, D-Arg²⁸, Har²⁹]hGH-RH(1-29)NH₂ |
| P-12714 | [(PhF₅Ac-Ada)⁰-Tyr¹, D-Arg², Cpa⁶, Ala⁸, Har⁹, Fpa5¹⁰, His¹¹, Orn¹², Leu¹³, Abu¹⁵, Glu¹⁷, His²⁰, Orn²¹, Nle²⁷, D-Arg²⁸, Har²⁹]hGH-RH(1-29)NH₂ |
| P-12716 | [(PhF₅Ac-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹]hGH-RH(1-29)NH₂ |
| P-12720 | [(CH₃—(CH₂)₁₀—CO-Ada)⁰-Tyr¹, D-Arg², Cpa⁶, Ala⁸, Har⁹, Fpa5¹⁰, His¹¹, Orn¹², Abu¹⁵, His²⁰, Orn²¹, Nle²⁷, D-Arg²⁸, Har²⁹]hGH-RH(1-29)NH₂ |
| P-12730 | [(PhAc-Ada)⁰-Tyr¹, D-Arg², Fpa5⁶, Ala⁸, Har⁹, Fpa5¹⁰, His¹¹, Orn¹², Abu¹⁵, Glu¹⁷, His²⁰, Orn²¹, Nle²⁷, D-Arg²⁸, Har²⁹]hGH-RH(1-29)NH₂ |
| P-12740 | [(PhAc-Ada)⁰-Tyr¹, D-Arg², Fpa5⁶, Ala⁸, Har⁹, Fpa5¹⁰, His¹¹, Orn¹², Abu¹⁵, Glu¹⁷, His²⁰, Orn²¹, Nle²⁷, D-Arg²⁸, Har²⁹, Ada³⁰]hGH-RH(1-30)NH₂ |
| P-12750 | [(PhAc-Ada)⁰-Tyr¹, D-Arg², Fpa5⁶, Ala⁸, Har⁹, Fpa5¹⁰, His¹¹, Orn¹², His¹⁵, Glu¹⁷, His²⁰, Orn²¹, Nle²⁷, D-Arg²⁸, Har²⁹]hGH-RH(1-29)NH₂ |
| P-12760 | [(CH₃—(CH₂)₁₀—CO-Ada)⁰-Tyr¹, D-Arg², Fpa5⁶, Ala⁸, Har⁹, Fpa5¹⁰, His¹¹, Orn¹², Abu¹⁵, Glu¹⁷, His²⁰, Orn²¹, Nle²⁷, D-Arg²⁸, Har²⁹]hGH-RH(1-29)NH₂ |
| P-12770 | [(Ac-Ada)⁰-Tyr¹, D-Arg², Fpa5⁶, Ala⁸, Har⁹, Fpa5¹⁰, His¹¹, Orn¹², Abu¹⁵, His²⁰, Orn²¹, Nle²⁷, D-Arg²⁸, Har²⁹]hGH-RH(1-29)NH₂ |
| P-12780 | [(PhF₅Ac-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Ada³⁰]hGH-RH(1-30)NH₂ |
| P-12800 | [(PhF₅Ac-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12802 | [(PhAc-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12804 | [(Ac-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12806 | [(CH₃—(CH₂)₁₀—CO-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12808 | [(Dca-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12810 | [(PhF₅Ac-Ada)⁰-Tyr¹, D-Arg², Fpa5⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12812 | [(PhAc-Ada)⁰-Tyr¹, D-Arg², Fpa5⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12814 | [(Ac-Ada)⁰-Tyr¹, D-Arg², Fpa5⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12816 | [(CH₃—(CH₂)₁₀—CO-Ada)⁰-Tyr¹, D-Arg², Fpa5⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12818 | [(Dca-Ada)⁰-Tyr¹, D-Arg², Fpa5⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Agm³⁰]hGH-RH(1-30) |
| P-12840 | [(PhF₅Ac-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Ada³⁰]hGH-RH(1-30)OH |
| P-12842 | [(PhAc-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Ada³⁰]hGH-RH(1-30)OH |
| P-12844 | [(Ac-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹, Ada³⁰]hGH-RH(1-30)OH |

TABLE A-continued

| | |
|---|---|
| P-12846 | [($CH_3$—($CH_2$)$_{10}$—CO-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12848 | [(Dca-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12850 | [PhF$_5$Ac$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12852 | [PhAc$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12854 | [Dca$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12860 | [(PhF$_5$Ac-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12862 | [(PhAc-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12864 | [(Ac-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12866 | [($CH_3$—($CH_2$)$_{10}$—CO-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12868 | [(Dca-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12870 | [PhF$_5$Ac$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12872 | [PhAc$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12874 | [Dca$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12880 | [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)$NH_2$ |
| P-12890 | [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-29)$NH_2$ |
| P-12900 | [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-29) |
| P-12920 | [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-29)OH |

C. Method of Preparation

Overview of Synthesis

The peptides are synthesized by suitable methods such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, Ill., 1984 (2nd. ed.), and M. Bodanszky, "Principles of Peptide Synthesis", Springer Verlag, 1984. The hGH-RH antagonist peptides are preferably prepared using solid phase synthesis, such as that generally described by Merrifield, J. Am. Chem. Soc., 85 p. 2149 (1963), although other equivalent chemical syntheses known in the art can also be used as previously mentioned.

The synthesis is carried out with amino acids that are protected at their alpha amino group. Urethane type protecting groups (Boc or Fmoc) are preferably used for the protection of the alpha amino group.

In solid phase synthesis, the N-alpha-protected amino acid moiety which forms the aminoacyl group of the final peptide at the C-terminus is attached to a polymeric resin support via a chemical link. After completion of the coupling reaction, the alpha amino protecting group is selectively removed to allow subsequent coupling reactions to take place at the amino-terminus, preferably with 50% TFA in DCM when the N-alpha-protecting group is Boc, or by 20% piperidine in DMF when the N-alpha-protecting group is Fmoc. The remaining amino acids in the sequence with similarly Boc or Fmoc-protected alpha amino groups are coupled stepwise to the free amino group of the preceding amino acid on the resin to obtain the desired peptide sequence. Because the amino acid residues are coupled to the alpha amino group of the C-terminus residue, growth of the synthetic hGH-RH analogue peptides begins at the C terminus and progresses toward the N-terminus. When the desired sequence has been obtained, the peptide is acylated at the N-terminus, and it is removed from the support polymer.

Each protected amino acid is used in excess (2.5 or 3 equivalents) and the coupling reactions are usually carried out in DCM, DMF or mixtures thereof. The extent of completion of the coupling reaction is monitored at each stage by the ninhydrin reaction. In cases where incomplete coupling is determined, the coupling procedure is repeated, or a capping by acetylation of unreacted amino groups is carried out, before removal of the alpha amino protecting group prior to the coupling of the next amino acid.

Typical synthesis cycles are shown in Table I and Table II.

TABLE I

Protocol for a Typical Synthetic Cycle Using Boc-strategy

| Step | Reagent | Mixing Time (min) |
|---|---|---|
| 1. Deprotection | 50% TFA in DCM | 5 + 25 |
| | DCM wash | 1 |
| | 2-propanol wash | 1 |
| 2. Neutralization | 5% DIEA in DCM | 1 |
| | DCM wash | 1 |
| | MeOH wash | 1 |
| | 5% DIEA in DCM | 3 |
| | MeOH wash | 1 |
| | DCM wash (3 times) | 1 |
| 3. Coupling | 3 eq. Boc-amino acid in DCM or DMF + 3 eq. DIC or the preformed HOBt ester of the Boc-amino acid | 90 |
| | MeOH wash (3 times) | 1 |
| | DCM wash (3 times) | 1 |
| 4. Acetylation (if appropriate) | Ac$_2$O in pyridine (30%) | 10 + 20 |
| | MeOH wash (3 times) | 1 |
| | DCM wash (3 times) | 1 |

TABLE II

Protocol for a Typical Synthetic Cycle Using Fmoc-strategy

| Step | Reagent | Mixing Time (min) |
|---|---|---|
| 1. Deprotection | 20% piperidine in DMF | 5 + 15 |
| | DMF wash (3 times) | 1 |
| 2. Coupling | 3 eq. Fmoc-amino acid in DMF + 3 eq. DIC or + 3 eq. HBTU + 3 eq. HOBt + 6 eq. DIEA | 90 |
| | DMF wash (3 times) | 1 |
| 3. Acetylation (if appropriate) | 3 eq. 1-acetylimidazole in DMF | 30 |
| | DMF wash (3 times) | 1 |

After completion of the synthesis, the cleavage of the peptide from the resin can be effected using procedures well known in peptide chemistry.

2. Choice of the Support Polymer.

The hGH-RH antagonist peptides may be synthesized on a variety of support polymers, i.e. MBHA, Merrifield, PAM, Rink amide or Wang resins. The peptides can also be synthesized on aminomethyl, MBHA, or other resins that have been previously derivatized with suitable linkers. Examples of such linkers are the base-labile 4-hydroxymethyl benzoic acid (HMBA) linker for the attachment of C-terminal carboxyl groups or the acid-labile para-sulfonyl-phenoxyacetyl (SPA) linker which permits the attachment of agmatine through its guanidino group.

When peptides with an amidated C-terminus are synthesized by using Boc strategy, the preferred resin is MBHA. Attachment of the C-terminal amino acid to this resin can be accomplished by the standard DIC-mediated coupling method described in Table I.

In order to prepare peptides with a C-terminal ethylamide (—NHEt) modification, the Merrifield resin or HMBA-MBHA resin can be used in conjunction with the Boc strategy. Loading of the C-terminal amino acid onto the Merrifield resin is done by coupling mediated by potassium fluoride (KF) or cesium salt at elevated temperature.

For the synthesis of peptides having Agm at the C-terminus, it is preferred that the support phase is MBHA resin or an aminomethyl resin. The guanidino group of Boc-Agm is joined to the support polymer through a stable, but readily cleavable linker such as the para-sulfonyl-phenoxyacetyl (SPA) moiety. The alpha-amino-Boc-protected Agm is reacted with the chlorosulfonyl phenoxyacetic acid Cl—SO$_2$—C$_6$H$_4$—O—CH$_2$—COOH to form Boc-Agm-SO$_2$—C$_6$H$_4$—O—CH$_2$—COOH. This compound is then coupled to the support polymer e.g. to MBHA resin using DIC or HBTU-HOBt-DIEA as activating reagent to yield Boc-Agm-SPA-MBHA.

3. Amino Acid Derivatives Used.

Bifunctional amino acids, i.e. those not having side chain functional groups, are mostly used in the form of their N-alpha Boc- or Fmoc-derivatives for synthesis.

Thus, Boc-Ala-OH or Fmoc-Ala-OH is typically used for incorporating the residue. The naturally occurring bifunctional α-amino acids are Gly, Ala, Val, Leu, Ile, Phe, and Pro, and some well-known non-coded bifunctional amino acids used in this invention are Abu, Aib, and Nle.

Some of the amino acid residues of the peptides have side chain functional groups which are reactive with reagents used in coupling or deprotection. When such side chain groups are present, suitable protecting groups are joined to these functional groups to prevent undesirable chemical reactions occurring during the reactions used to form the peptides. The following general rules are followed in selecting a particular side chain protecting group: (a) the protecting group preferably retains its protecting properties and is not split off under coupling conditions, (b) the protecting group should be stable under conditions for removing the alpha amino protecting group at each step of the synthesis, (c) the side chain protecting group must be removable upon the completion of the synthesis of the desired amino acid sequence, under reaction conditions that will not undesirably alter the peptide chain.

When Boc-amino acids are used in the synthesis, the reactive side chain functional groups can be protected as follows: Tos or nitro (NO$_2$) for Arg and Har; cHx or Fm for Asp and Glu; Bom for His; 2ClZ or Fmoc for Lys and Orn; Bzl for Ser and Thr; and 2BrZ for Tyr. The side chains of Asn and Gln are unprotected. In the case of Fmoc synthesis, the reactive side chain functional groups can be protected by other appropriate protective groups as follows: 2,2,4,6,7-pentamethyl-dihydrobenzofurane-5-sulfonyl (Pbf) or bis-Boc for Arg and Har; tert-butyl (tBu) for Asp and Glu; no protective group or trityl (Trt) protection for Asn and Gln; Trt for His; Boc or 4-methoxytrityl (Mmt) for Lys and Orn; tBu or Trt for Ser and Thr; and tBu or 2-chlorotrityl (2ClTrt) for Tyr. In addition to the widely known coded and non-coded amino acids mentioned above, some of the peptides of this application contain less common non-coded amino acids such as para-amidino-phenylalanine (Amp); para-guanidino-phenylalanine (Gup); 1,2,3,4-tetrahydronorharman-3-carboxylic acid (Tpi); (2-naphthyl)alanine (2-Nal); (3,3-diphenyl)alanine (Dip); para-amino-phenylalanine [Phe(pNH$_2$)]; para-nitro-phenylalanine [Phe(pNO$_2$)]; (3-pyridyl)alanine (3-Pal); O-ethyl-tyrosine [Tyr(Et)]; and mono-, di-, or polyfluorinated Phe (Fpa, Fpa2, Fpa3, Fpa4, Fpa5). These amino acid residues are incorporated into the peptides by coupling the suitable protected amino acid derivatives. A non-exclusive list of such protected amino acid derivatives that can be used is as follows: Boc-Amp(Alloc)-OH, Boc-Amp-OH, Fmoc-Amp(Alloc)-OH, Fmoc-Amp-OH, Boc-Gup(Tos)-OH, Boc-Gup-OH, Fmoc-Gup(Boc)$_2$-OH, Fmoc-Gup-OH, Boc-Cha-OH, Boc-Tpi-OH, Boc-2-Nal-OH, Boc-Dip-OH, Boc-Phe (pNH—Z)—OH, Boc-Phe(pNO$_2$)—OH, Boc-3-Pal-OH, Boc-Tyr(Et)-OH, Boc-Bpa-OH Boc-Fpa-OH, Boc-Fpa2-OH, Boc-Fpa3-OH, Boc-Fpa-4-OH, Boc-Fpa5-OH. Most of the protected derivatives of noncoded amino acids mentioned above are commonly available from several commercial suppliers, including Bachem (King of Prussia, Pa.), Peptides International (Louisville, Ky.), Novabiochem (San Diego, Calif.), Advanced ChemTech (Louisville, Ky.), and RSP Amino Acid Analogues DBA (Worcester, Mass.).

4. Stepwise Coupling of Amino Acid Residues

Utilizing the above mentioned support polymers and after loading of the C-terminal amino acid or Agm residue, the peptide itself may suitably be built up by solid phase synthesis in the conventional manner. Each protected amino acid is coupled in about a three-fold molar excess, with respect to resin-bound free amino residues, and the coupling may be carried out in a medium such as DMF-DCM (1:1) or in DMF or DCM alone. The selection of an appropriate coupling reagent is within the skill of the art. Particularly suitable as coupling reagents are N,N'-diisopropyl carbodiimide (DIC), or HBTU combined with HOBt in the presence of DIEA. The success of the coupling reaction at each stage of the synthesis is preferably monitored by the ninhydrin reaction. In cases where incomplete coupling occurs, either the coupling procedure is repeated, or the resin-bound unreacted amino residues are acetylated using a capping reagent, before removal of the alpha amino protecting group. Suitable capping reagents are 1-acetylimidazole and Ac$_2$O-pyridine.

Final acylation of the N-terminus of the peptide with monocarboxylic acids is done in the same way as the previous couplings, with the difference that the appropriate carboxylic acid is used instead of an amino acid. When dicarboxylic acids are attached to the N-terminus and it is desired that only one —COOH group reacts with the amino terminus of the peptide (that is, monoamides of these acids are prepared), the anhydrides of the respective dicarboxylic acids can be used for coupling. The cyclic anhydrides of many dicarboxylic acids are commercially available; in other cases the preformed anhydrides of these acids are prepared by treatment with DIC and used for coupling.

5. Cleavage of the Peptide from the Support Polymer and Removal of the Side-Chain Protecting Groups When the synthesis is complete, the peptide is cleaved from the support phase and its side-chain protecting groups are removed.

In cases where peptides with an amidated C-terminus (—CONH$_2$) or with a C-terminal carboxyl group (—COOH) are prepared by Boc strategy on an MBHA, Merrifield, or PAM resin, the removal of the peptide from the resin is performed by treatment with a reagent such as liquid hydrogen fluoride (HF). This is also the case for peptides synthesized on the Boc-Agm-SPA-MBHA resin. In some instances, the liquid HF also cleaves all the remaining side chain protecting groups. However, if side chain protecting groups resistant to HF treatment are present on the peptide, additional cleavage steps should be performed in order to remove these protecting groups. Thus, Fm and Fmoc protecting groups are removed by treatment with 20% piperidine in DMF, while All and Alloc groups are removed by treatment with Pd(PPh$_3$)$_4$ catalyst and nucleophilic scavengers, prior to or after the HF treatment.

Suitably, the dried and protected peptide-resin is treated with a mixture consisting of 1.0 mL m-cresol and 10 mL anhydrous hydrogen fluoride per gram of peptide-resin for 60-120 min at 0° C. to cleave the peptide from the resin as well as to remove the HF-labile side chain protecting groups. After the removal of the hydrogen fluoride under a stream of nitrogen and vacuum, the free peptides are precipitated with ether, filtered, washed with ether and ethyl acetate, extracted with 50% acetic acid, and lyophilized.

In cases where peptides with an ethylamide (—NHEt) C-terminus are prepared by Boc strategy on the Merrifield or HMBA-MBHA resin, the protected peptides are first cleaved from the resin by ethylamine (EtNH$_2$) mediated aminolysis. Suitably, liquid EtNH$_2$ is transferred into a cooled, heavy-walled glass flask that contains the dried and protected peptide-resin. The quantity of liquid EtNH$_2$ should be sufficient to cover the peptide-resin. The flask is stoppered, and shaken with the liquid EtNH$_2$ for 3.5 hours at room temperature in order to allow for the reaction to take place. After this, the flask is cooled in a dry ice bath, opened, and the liquid EtNH$_2$ is filtered off the solid residue that contains a mixture of resin and cleaved peptide, the peptide still having the protecting groups attached. The solid residue is dried and subjected to HF treatment as described above, in order to remove the side chain protecting groups of the peptide.

6. Purification.

The purification of the crude peptides can be effected using procedures well known in peptide chemistry. For example, purification may be performed on a MacRabbit HPLC system (Rainin Instrument Co. Inc., Woburn, Mass.) with a Knauer UV Photometer and a Kipp and Zonen BD40 Recorder using a Vydac 218TP510 reversed-phase column (10×250 mm, packed with C18 silica gel, 300 Å pore size, 5 µm particle size) (The Separations Group Inc., Hesperia, Calif.). The column is eluted with a solvent system consisting of (A) 0.1% aqueous TFA and (B) 0.1% TFA in 70% aqueous MeCN in a linear gradient mode (e.g., 30-55% B in 120 min). The eluent is monitored at 220 nm, and fractions are examined by analytical HPLC using a Hewlett-Packard Model HP-1090 liquid chromatograph and pooled to give maximum purity. Analytical HPLC is carried out on a Vydac 218TP52 reversed-phase column (2×250 mm, C18, 300 Å, 5 µm) using isocratic elution with a solvent system consisting of (A) and (B) defined above. The peaks are monitored at 220 and 280 nm. The peptides are judged to be substantially (>95%) pure by analytical HPLC. Molecular masses are checked by electrospray mass spectrometry, and the expected amino acid compositions are confirmed by amino acid analysis.

D. Pharmaceutical Compositions and Mode of Administration.

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, trifluoroacetate, citrate, benzoate, succinate, alginate, pamoate, malate, ascorbate, tartarate, and the like. Particularly preferred antagonists are salts of low solubility, e.g., pamoate salts and the like. These exhibit long duration of activity.

The compounds of the present invention are suitably administered to subject humans or animals subcutaneously (s.c.), intramuscularly (i.m.), or intravenously (i.v); intranasally or by pulmonary inhalation; by transdermal delivery; or in a depot form (e.g., microcapsules, microgranules, or cylindrical rod like implants) formulated from a biodegradable suitable polymer (such as D,L-lactide-coglycolide), the former two depot modes being preferred. Other equivalent modes of administration are also within the scope of this invention, i.e., continuous drip, cutaneous patches, depot injections, infusion pump and time release modes such as microcapsules and the like. Administration is in any physiologically acceptable injectable carrier, physiological saline being acceptable, though other carriers known to the art may also be used.

The peptides are preferably administered parenterally, intramuscularly, subcutaneously or intravenously with a pharmaceutically acceptable carrier such as isotonic saline. Alternatively, the peptides may be administered as an intranasal spray with an appropriate carrier or by pulmonary inhalation. One suitable route of administration is a depot form formulated from a biodegradable suitable polymer, e.g., poly-D,L-lactide-coglycolide as microcapsules, microgranules or cylindrical implants containing dispersed antagonistic compounds.

The amount of peptide needed depends on the type of pharmaceutical composition and on the mode of administration. In cases where human subjects receive solutions of GH-RH antagonists, administered by i.m. or s.c. injection, or in the form of intranasal spray or pulmonary inhalation, the typical doses are between 2-20 mg/day/patient, given once a day or divided into 2-4 administrations/day. When the GH-RH antagonists are administered intravenously to human patients, typical doses are in the range of 8-80 µg/kg of body weight/day, divided into 1-4 bolus injections/day or given as a continuous infusion. When depot preparations of the GH-RH antagonists are used, e.g. by i.m. injection of pamoate salts or other salts of low solubility, or by i.m. or s.c. administration of microcapsules, microgranules, or implants containing the antagonistic compounds dispersed in a biodegradable polymer, the typical doses are between 1-10 mg antagonist/day/patient.

E. Therapeutic Uses of GH-RH Antagonists.

The most important therapeutic applications of GH-RH antagonists are expected to be in the field of oncology and endocrinology. Some of the GH-RH antagonists act predominantly at the pituitary level and have stronger endocrine effects, inhibiting the GH-RH-evoked GH release, and ultimately decreasing the serum levels of GH and IGF-I. Other GH-RH antagonists act predominantly at the tumor level, by blocking the tumoral receptors for GH-RH, reducing the production of various autocrine/paracrine tumor growth factors (such as IGF-I, IGF-II, GH, VEGF, FGF) and/or downregulating their receptors, and thus exert stronger inhibitory effects on tumor growth. These antagonists can also be used as carrier systems linked to radionuclides for tumor localization or therapy, or conjugated to chemotherapeutic agents or toxins. Such hybrid compounds can be actively targeted to cancer for diagnostic or therapeutic purposes. Yet other GH-RH antagonists act by multiple mechanisms of action, that is by endocrine mechanisms and by direct effects on tumors at the same time. Thus, the main therapeutic indications of various GH-RH antagonists differ based on their preferential mechanism of action.

Analogs of GH-RH with antagonistic action on the pituitary can be used in situations where it is beneficial to suppress serum levels of GH and IGF-I. Thus they are indicated for the therapy of endocrine disorders characterized by excessive production of GH and IGF-I, as well as for the treatment of cancers that express receptors for IGF-I, IGF-II, or GH, and the proliferation of which is stimulated by these growth factors.

Somatostatin analogs and GH antagonists are also available for the treatment of endocrine conditions caused by GH and IGF-I. However, GH-RH antagonists offer unique therapeutical benefits unobtainable by the use of somatostatin analogs and GH antagonists.

These benefits are due to the multiple mechanisms of action of GH-RH antagonists, namely that they exert GH- and IGF-I-independent direct effects on tumors and other target sites, in addition to inhibiting the endocrine axis for GH and IGF-I. GH-RH antagonists may be given alone or together with somatostatin analogs, a combination which more completely suppresses GH and IGF-I levels. An undesired side-effect of GH antagonists, which can be avoided by the administration of GH-RH antagonists, is the elevation of serum GH levels through a feed-back mechanism.

One disease caused by excess growth hormone is acromegaly, which is manifested in an abnormal enlargement of the bones of the face and extremities. GH-RH antagonists could alleviate the clinical manifestations of acromegaly, e.g. the enlargement of facial and extremity bones, the enlargement of heart, and other structural and functional abnormalities of the cardiovascular system. The GH-RH antagonists may also be used to treat diabetic retinopathy (the main cause of blindness in diabetics) and diabetic nephropathy, in which damage to the eye and kidney respectively is thought to be due to GH. Diabetic patients can also benefit from the increased insulin sensitivity produced by GH-RH antagonists, an effect linked to the ability of these compounds to reduce the GH and IGF-I levels. In addition, since they inhibit GH release, GH-RH antagonists can be used to slow down the progression of muscular dystrophy.

Drugs with anti-growth factor properties such as GH-RH antagonists can also be of benefit in controlling or slowing down the progression of some clinicopathologic processes in conditions such as idiopathic pulmonary fibrosis, systemic sclerosis and hypertrophic cardiomyopathy, where the present medical therapies have relatively little to offer.

GH-RH antagonists may be administered to decrease the occurrence of restenosis of various vessels and synthetic stents and devices such as stents in percutaneous transluminal coronary angioplasty (PTCA). This decrease is achieved by administering to said patient an effective amount of a suitable GHRH antagonist such as compound of claim 1 sufficient to provide such decrease. The restenosis can occur as a result of many conditions.

Of particular interest is that caused by the prior insertion of a therapeutically effective device into an appropriate location in the patient, for example where the device is a stent in particular where the stent is a synthetic stent especially where stent is inserted as part of the process of percutaneous angioplasty. The method is usefully employed when restenosis occurs during dialysis of a patient, in such a case the compound is administered in the dialysis fluid. Incorporation of GHRH antagonists into or onto the surfaces of such devices is also within the scope of the present invention. For example the compound may coated onto the surface of the device or incorporated into the device.

Some gynecologic conditions, such as myoma, endometriosis, and polycystic ovary syndrome, can also be treated with GH-RH antagonists in combination with luteinizing hormone-releasing hormone (LH-RH) agonists or antagonists. GH-RH antagonists are also available for treatment of benign prostatic hyperplasia (BPH), and hyperplastic and benign proliferative disorders of other normal organs in which the GH-RH receptors are present.

However, the main applications of GH-RH antagonists are in the field of cancer. GH-RH antagonists, especially those with strong direct effects at the tumor level, are indicated for the inhibition of growth of primary tumors and for the suppression of their metastatic spread. Since the antiproliferative effects of GH-RH antagonists are exerted by several mechanisms, these compounds are available for the treatment of a large variety of cancers, such as those that depend on autocrine/paracrine and endocrine stimulation by GH-RH, IGF-I, IGF-II, GH, VEGF, and FGF.

GH-RH antagonists are available for the treatment of tumors that express GH-RH receptors and use GH-RH as an autocrine/paracrine growth factor. Such malignancies include, but are not limited to, cancers of the lung, prostate, breast, ovary, endometrium, stomach, intestine, pancreas, kidney, bone, liver, as well as glioblastomas, pheochromocytomas, melanomas, and lymphomas. By blocking the tumoral receptors for GH-RH, these antagonists prevent the stimulatory action of GH-RH, resulting in inhibition of tumor growth.

One advantage of GH-RH antagonists over somatostatin analogs is based on the fact that GH-RH antagonists may be utilized for suppression of tumors which do not have somatostatin receptors but express the tumoral receptors for GH-RH, for example human osteogenic sarcomas.

Malignancies that express the IGF-I receptors, and depend on IGF-I and/or IGF-II as growth factors, are available for therapy with GH-RH antagonists. These malignancies include, among others, lung cancers, prostatic, breast, ovarian, endometrial, gastric, colorectal, pancreatic, renal, and hepatic cancers, sarcomas, and brain tumors. The ability of GH-RH antagonists to decrease serum IGF-I levels, inhibit the autocrine/paracrine production of IGF-I and/or IGF-II in the tumor tissue, and downregulate the expression level of IGF-I receptor, is beneficial for cancer therapy.

Breast cancers and other types of cancer that depend on GH as a growth factor, can be treated with GH-RH antagonists. The ability of GH-RH antagonists to reduce serum GH levels, inhibit the autocrine production of GH, and downregulate GH receptor expression, beneficiate the treatment of certain breast cancers and other types of tumors as well.

GH-RH antagonists are available as inhibitors of angiogenesis, in view of their inhibitory activity on the synthesis of VEGF by tumor tissues and normal endothelial cells, and considering their antiproliferative effect on endothelial cells. Thus GH-RH antagonists could be beneficial for the treatment of those tumors that strongly depend on VEGF and neoangiogenesis.

EXAMPLES

The present invention is described in connection with the following examples which are set forth for the purposes of illustration only. In the examples, optically active protected amino acids in the L-configuration are used except where specifically noted.

The following Examples set forth suitable methods of synthesizing the novel GH-RH antagonists by the solid-phase technique.

Example I

PhAc$^0$-Tyr$^1$-D-Arg$^2$-Asp$^3$-Ala$^4$-Ile$^5$-Cpa$^6$-Thr$^7$-Ala$^8$-Har$^9$-Fpa5$^{10}$-His$^{11}$-Orn$^{12}$-Val$^{13}$-Leu$^{14}$-Abu$^{15}$-Gln$^{16}$-Leu$^{17}$-Ser$^{18}$-Ala$^{19}$-His$^{20}$-Orn$^{21}$-Leu$^{22}$-Leu$^{23}$-Gln$^{24}$-Asp$^{25}$-Ile$^{26}$-Nle$^{27}$-D-Arg$^{28}$-Har$^{29}$-Ada$^{30}$-NH$_2$ (Peptide 12610)

[PhAc$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$, Ada$^{30}$]hGH-RH(1-30)NH$_2$

The synthesis is conducted in a stepwise manner using manual solid phase peptide synthesis equipment. Briefly, para-methylbenzhydrylamine (MBNA) resin (Bachem, King of Prussia, Pa.) (720 mg, 0.50 mmol) is neutralized with 5% DIEA in DCM and washed according to the protocol described in Table I. The solution of Boc-Ada-OH (473 mg, 1.5 mmol) in DMF-DCM (1:1) is shaken with the neutralized resin and DIC (235 μL, 1.5 mmol) in a manual solid phase peptide synthesis apparatus for 1.5 hour. After the completion of the coupling reaction is proved by negative ninhydrin test, the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Har(NO$_2$)$_2$—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

These protected amino acid residues (also commonly available from Bachem, Novabiochem, Advanced Chemtech, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 μL, 1.5 mmol) with the exceptions of Boc-Asn-OH and Boc-Gln-OH which are coupled with their preformed HOBt esters.

In order to cleave the peptide from the resin and deprotect it, a portion of 600 mg of the dried peptide resin is stirred with 0.6 mL m-cresol and 6 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 132 mg crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 μm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 135 mg of crude peptide is dissolved in AcOH/H$_2$O, stirred, filtered and applied on a Beckman Ultraprep ODS column (21.2 mm×15 cm, packed with C18 silica gel, 300 Å pore size, 10 μm particle size). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 10.2 mg pure product. The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 12640, Peptide 12642, Peptide 12644, Peptide 12652, Peptide 12654, Peptide 12656, Peptide 12660, Peptide 12662, Peptide 12664, Peptide 12666, Peptide 12670, Peptide 12672, Peptide 12674, Peptide 12740, Peptide 12780, and Peptide 12890 are synthesized in the same manner as Peptide 12610, except that these peptides also contain other amino acid substitutions in the peptide sequence and other acyl moieties at their N-termini. The details for these syntheses are set forth below.

For the synthesis of Peptide 12640, the chemical structure of which is [PhAc$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 12642, the chemical structure of which is [PhAc$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 12644, the chemical structure of which is [PhAc$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH. For the synthesis of Peptide 12660, the chemical structure of which is [PhAc$^0$-Tyr$^1$, D-Arg$^2$, Cpa$^6$, Ala$^8$, Har$^9$, Fpa5$^{10}$, His$^{11}$, Orn$^{12}$, His$^{15}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 12662, the chemical structure of which is [PhAc$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 12670, the chemical structure of which is [PhAc$^0$-Tyr$^1$, D-Arg$^2$, Fpa5$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 12890, the chemical structure of which is [PhAc$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Fpa5-OH, followed by acylation with PhAc-OH.

For the synthesis of Peptide 12652, the chemical structure of which is [PhF$_5$Ac$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12654, the chemical structure of which is [PhF$_5$Ac$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12656, the chemical structure of which is [PhF$_5$Ac$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2CIZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12664, the chemical structure of which is [PhF$_5$Ac$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12672, the chemical structure of which is [PhF$_5$Ac$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2CIZ)-OH, Boc-His(Bom)-OH, Boc-Fpa5-OH, Boc-Har(NO$_2$)—OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12674, the chemical structure of which is [PhF$_5$Ac$^0$-Tyr$^1$, D-Arg$^2$, Fpa5$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har(NO$_2$)—OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12666, the chemical structure of which is [(PhAc-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har(NO$_2$)—OH, Boc-Ala-OH, Boc-Thr(Bzl)-OH, Boc-Fpa5-OH, Boc-Ile-OH, Boc-(Me-Ala)-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12740, the chemical structure of which is [(PhAc-Ada)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2CIZ)-OH, Boc-His(Bom)-OH, Boc-Fpa5-OH, Boc-Har(NO$_2$)—OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12780, the chemical structure of which is [PhF$_5$Ac-Ada$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-Ada-OH

Example II

Ac-Ada⁰-Tyr¹-D-Arg²-Asp³-Ala⁴-Ile⁵-Cpa⁶-Thr⁷-
Ala⁸-Har⁹-Fpa5¹⁰-His¹¹-Orn¹²-Val¹³-Leu¹⁴-Abu¹⁵-
Gln¹⁶-Leu¹⁷-Ser¹⁸-Ala¹⁹-His²⁰-Orn²¹-Leu²²-Leu²³-
Gln²⁴-Asp²⁵-Ile²⁶-Nle²⁷-D-Arg²⁸-Har²⁹-NH₂

(Peptide 12680)

[(Ac-Ada⁰-Tyr¹, D-Arg², Cpa⁶, Ala⁸, Har⁹, Fpa5¹⁰, His¹¹, Orn¹², Abu¹⁵, His²⁰, Orn²¹, Nle²⁷, D-Arg²⁸, Har²⁹]hGH-RH(1-29)NH₂

The synthesis is conducted in a stepwise manner using manual solid phase peptide synthesis equipment. Briefly, para-methylbenzhydrylamine (MBNA) resin (Bachem, King of Prussia, Pa.) (720 mg, 0.50 mmol) is neutralized with 5% DIEA in DCM and washed according to the protocol described in Table I. The solution of Boc-Har(NO₂)—OH (333 mg, 1.5 mmol) in DMF-DCM (1:1) is shaken with the neutralized resin and DIC (235 μL, 1.5 mmol) in a manual solid phase peptide synthesis apparatus for 1 hour. After the completion of the coupling reaction is proved by negative ninhydrin test, the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Fpa5-OH, Boc-Har(NO₂)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Ac-Ada-OH.

These protected amino acid residues (also commonly available from Bachem, Novabiochem, Advanced Chemtech, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 μL, 1.5 mmol) with the exceptions of Boc-Asn-OH and Boc-Gln-OH which are coupled with their preformed HOBt esters.

In order to cleave the peptide from the resin and deprotect it, a portion of 500 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 167 mg crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 μm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 135 mg of crude peptide is dissolved in AcOH/H₂O, stirred, filtered and applied on a Beckman Ultraprep ODS column (21.2 mm×15 cm, packed with C18 silica gel, 300 Å pore size, 10 μm particle size). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 19.8 mg pure product. The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 12682, Peptide 12684, Peptide 12690, Peptide 12692, Peptide 12694, Peptide 12696, Peptide 12698, Peptide 12710, Peptide 12712, Peptide 12714, Peptide 12716, Peptide 12720, Peptide 12730, Peptide 12750, Peptide 12760, Peptide 12770, and Peptide 12880, are synthesized in the same manner as Peptide 12680, except that these peptides also contain other amino acid substitutions in the peptide sequence and other acyl moieties at their N-termini. The details for these syntheses are set forth below.

For the synthesis of Peptide 12682, the chemical structure of which is [(Ac-Ada)⁰-Tyr¹, D-Arg², Cpa⁶, Ala⁸, Har⁹, Fpa5¹⁰, His¹¹, Orn¹², His¹⁵, Glu¹⁷, His²⁰, Orn²¹, Nle²⁷, D-Arg²⁸, Har²⁹]hGH-RH(1-29)NH₂, the following protected amino acids are coupled in the indicated order on the MBHA resin: Boc-Har(NO₂)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har(NO₂)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Ac-Ada-OH.

For the synthesis of Peptide 12684, the chemical structure of which is [(Ac-Ada)⁰-Tyr¹, D-Arg², Cpa⁶, (Me-Ala)⁸, Har⁹, Fpa5¹⁰, His¹¹, Orn¹², His¹⁵, Glu¹⁷, His²⁰, Orn²¹, Nle²⁷, D-Arg²⁸, Har²⁹]hGH-RH(1-29)NH₂, the following protected amino acids are coupled in the indicated order on the MBHA resin: Boc-Har(NO₂)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har(NO₂)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Ac-Ada-OH.

For the synthesis of Peptide 12690, the chemical structure of which is [(PhAc-Ada)⁰-Tyr¹, D-Arg², Cpa⁶, Ala⁸, Har⁹, Fpa5¹⁰, His¹¹, Orn¹², Abu¹⁵, His²⁰, Orn²¹, Nle²⁷, D-Arg²⁸, Har²⁹]hGH-RH(1-29)NH₂, the following protected amino acids are coupled in the indicated order on the MBHA resin: Boc-Har(NO₂)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Fpa5-OH, Boc-Har(NO₂)—OH, Boc-Ala-OH, Boc-Thr(Bzl)-OH, Boc-Cpa- OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12694, the chemical structure of which is [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12696, the chemical structure of which is [(PhAc-Ada$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12698, the chemical structure of which is [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12710, the chemical structure of which is [(PhAc-Ada)$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12712, the chemical structure of which is [(PhAc-Ada)$^0$-Tyr$^1$, D-Arg$^2$, Cpa$^6$, Ala$^8$, Har$^9$, Fpa5$^{10}$, His$^{11}$, Orn$^{12}$, Leu$^{13}$, Abu$^{15}$, Glu$^{17}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Leu-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12714, the chemical structure of which is [PhF$_5$Ac$^0$-Tyr$^1$, D-Arg$^2$, Cpa$^6$, Ala$^8$, Har$^9$, Fpa5$^{10}$, His$^{11}$, Orn$^{12}$, Leu$^{13}$, Abu$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Leu-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12716, the chemical structure of which is [(PhF$_5$Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-Ada-OH.

For the synthesis of Peptide 12730, the chemical structure of which is [(PhAc-Ada)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12750, the chemical structure of which is [(PhAc-Ada)$^0$-Tyr$^1$, D-Arg$^2$, Fpa5$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr (Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12770, the chemical structure of which is [(Ac-Ada)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn (2ClZ)-OH, Boc-His(Bom)-OH, Boc-Fpa5-OH, Boc-Har(NO$_2$)—OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with Ac-Ada-OH.

For the synthesis of Peptide 12650, the chemical structure of which is [PhF$_5$Ac$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn (2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-Ada-OH For the synthesis of Peptide 12692, the chemical structure of which is [(PhF$_5$Ac-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29) NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp (OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-Ada-OH.

For the synthesis of Peptide 12720, the chemical structure of which is [(CH$_3$—(CH$_2$)$_{10}$—CO-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with (CH$_3$—(CH$_2$)$_{10}$—CO-Ada-OH.

For the synthesis of Peptide 12760, the chemical structure of which is [(CH$_3$—(CH$_2$)$_{10}$—CO-Ada)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg (Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr (Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with (CH$_3$—(CH$_2$)$_{10}$—CO-Ada-OH.

For the synthesis of Peptide 12712, the chemical structure of which is [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His (Bom)-OH, Boc-Ala-OH, Boc-Ser(Bzl)-OH, Boc-Glu (OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12880, the chemical structure of which is [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His (Bom)-OH, Boc-Ala-OH, Boc-Ser(Bzl)-OH, Boc-Glu (OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr (Bzl)-OH, Boc-Cpa-OH, Boc-Ile-OH, Boc-Ala-OH, Boc-Asp(OcHx)-OH, Boc-D-Arg(Tos)-OH, Boc-Fpa5-OH, followed by acylation with PhAc-Ada-OH.

Example III (PhF$_5$Ac-Ada)$^0$-Tyr$^1$-D-Arg$^2$-Asp$^3$-Ala$^4$-Ile$^5$-Cpa$^6$-Thr$^7$-(Me-Ala)$^8$-Har$^9$-Fpa5$^{10}$-His$^{11}$-Orn$^{12}$-Val$^{13}$-Leu$^{14}$-His$^{15}$-Gln$^{16}$-Glu$^{17}$-Ser$^{18}$-Ala$^{19}$-His$^{20}$-Orn$^{21}$-Leu$^{22}$-Leu$^{23}$-Gln$^{24}$-Asp$^{25}$-Ile$^{26}$-Nle$^{27}$-D-Arg$^{28}$-Har$^{29}$-Agm$^{30}$ (Peptide 12800)

[(PhF$_5$Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30)

The synthesis is conducted in a stepwise manner using manual solid phase peptide synthesis equipment. The starting material of the synthesis is Boc-agmatine-N$^G$-sulfonyl-phenoxyacetyl-MBNA (Boc-Agm-SPA-MBHA) resin with a substitution of 0.3 mmol/g, which was obtained commercially from California Peptide Research, Inc. (Napa, Calif.). The synthesis of this resin has been described in U.S. Pat. No. 4,914,189 and in the scientific literature (Zarandi M, Serfozo P, Zsigo J, Bokser L, Janaky T, Olsen D B, Bajusz S, Schally A V, Int. J. Peptide Protein Res. 39: 211-217, 1992), hereby incorporated by reference. Briefly, Boc-Agm-SPA-MBHA resin (1.67 g, 0.50 mmol) is pre-swollen in DCM and then the deprotection and neutralization protocols described in Table I are performed in order to remove the Boc protecting group and prepare the peptide-resin for coupling of the next amino acid. After the completion of the coupling reaction is proved by negative ninhydrin test, the deprotection and neutralization protocols described in Table I are performed, and the synthesis is continued. The peptide chain is built stepwise by coupling the following protected amino acids in the indicated order on the Agm-SPA-MBHA resin to obtain the desired peptide sequence: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har($NO_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-Ada-OH.

These protected amino acid residues (also commonly available from Bachem, Novabiochem, Advanced Chemtech, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 µL, 1.5 mmol) with the exceptions of Boc-Asn-OH and Boc-Gln-OH which are coupled with their preformed HOBt esters.

In order to cleave the peptide from the resin and deprotect it, a portion of 500 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 127 mg crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 µm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 135 mg of crude peptide is dissolved in AcOH/$H_2O$, stirred, filtered and applied on a Beckman Ultraprep ODS column (21.2 mm×15 cm, packed with C18 silica gel, 300 Å pore size, 10 µm particle size). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 11.3 mg pure product. The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 12802, Peptide 12804, Peptide 12806, Peptide 12808, Peptide 12810, Peptide 12812, Peptide 12814, Peptide 12816, Peptide 12818, and Peptide 12900 are synthesized in the same manner as Peptide 12800, except that these peptides also contain other amino acid substitutions in the peptide sequence and other acyl moieties at their N-termini. The details for these syntheses are set forth below.

For the synthesis of Peptide 12802, the chemical structure of which is [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30), the following protected amino acids are coupled in the indicated order on the Agm-SPA-MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har($NO_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12804, the chemical structure of which is [(Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30), the following protected amino acids are coupled in the indicated order on the Agm-SPA-MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har($NO_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Ac-Ada-OH.

For the synthesis of Peptide 12806, the chemical structure of which is [($CH_3$—$(CH_2)_{10}$—CO-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30), the following protected amino acids are coupled in the indicated order on the Agm-SPA-MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har($NO_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with ($CH_3$—$(CH_2)_{10}$—CO-Ada-OH.

For the synthesis of Peptide 12808, the chemical structure of which is [(Dca-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30), the following protected amino acids are coupled in the indicated order on the Agm-SPA-MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2CIZ)-OH, Boc-His(Bom)-OH, Boc-Fpa5-OH, Boc-Har($NO_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Dca-Ada-OH.

For the synthesis of Peptide 12810, the chemical structure of which is [(PhF$_5$Ac-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30), the following protected amino acids are coupled in the indicated order on the Agm-SPA-MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-Ada-OH.

For the synthesis of Peptide 12812, the chemical structure of which is [(PhAc-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30), the following protected amino acids are coupled in the indicated order on the Agm-SPA-MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12814, the chemical structure of which is [(Ac-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30), the following protected amino acids are coupled in the indicated order on the Agm-SPA-MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with Ac-Ada-OH.

For the synthesis of Peptide 12816, the chemical structure of which is [(CH$_3$—(CH$_2$)$_{10}$—CO-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30), the following protected amino acids are coupled in the indicated order on the Agm-SPA-MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with (CH$_3$—(CH$_2$)$_{10}$—CO-Ada-OH.

For the synthesis of Peptide 12900, the chemical structure of which is [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$hG-RH(1-30), the following protected amino acids are coupled in the indicated order on the Agm-SPA-MBHA: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Fpa5-OH, followed by acylation with PhAc-Ada-OH.

Example IV (PhF$_5$Ac-Ada)$^0$-Tyr$^1$-D-Arg$^2$-Asp$^3$-Ala$^4$-Ile$^5$-Cpa$^6$-Thr$^7$-(Me-Ala)$^8$-Har$^9$-Fpa5$^{10}$-His$^{11}$-Orn$^{12}$-Val$^{13}$-Leu$^{14}$-His$^{15}$-Gln$^{16}$-Glu$^{17}$-Ser$^{18}$-Ala$^{19}$-His$^{20}$-Orn$^{21}$-Leu$^{22}$-Leu$^{23}$-Gln$^{24}$-Asp$^{25}$-Ile$^{26}$-Nle$^{27}$-D-Arg$^{28}$-Har$^{29}$-Ada$^{30}$-OH (Peptide 12840)

[(PhF$_5$Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH

The synthesis is conducted in a stepwise manner using manual solid phase peptide synthesis equipment. Briefly, Boc-Ada-Merrifield resin (NovaBiochem, USA) (1.00 g, 0.50 mmol) is pre-swollen in DCM and then the deprotection and neutralization protocols described in Table I are performed in order to remove the Boc protecting group and prepare the peptide-resin for coupling of the next amino acid. After the completion of the coupling reaction is proved by negative ninhydrin test, the deprotection and neutralization protocols described in Table I are performed. The synthesis is continued and the peptide chain is built stepwise by coupling the following protected amino acids in the indicated order on the Ada-Merrifield resin to obtain the desired peptide sequence: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-Ada-OH.

These protected amino acid residues (also commonly available from Bachem, Novabiochem, Advanced Chemtech, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 μL, 1.5 mmol) with the exceptions of Boc-Asn-OH and Boc-Gln-OH which are coupled with their preformed HOBt esters.

In order to cleave the peptide from the resin and deprotect it, a portion of 500 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 107 mg crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 μm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 135 mg of crude peptide is dissolved in AcOH/H$_2$O, stirred, filtered and applied on a Beckman Ultraprep ODS column (21.2 mm×15 cm, packed with C18 silica gel, 300 Å pore size, 10 μm particle size). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 11.3 mg pure product. The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 12842, Peptide 12844, Peptide 12846, Peptide 12848, Peptide 12850, Peptide 12852, Peptide 12854, Peptide 12860, Peptide 12862, Peptide 12864, Peptide 12866, Peptide 12868, Peptide 12870, Peptide 12872, Peptide 12874, and Peptide 12920 are synthesized in the same manner as Peptide 12842, except that these peptides also contain other amino acid substitutions in the peptide sequence and other acyl moieties at their N-termini. The details for these syntheses are set forth below.

For the synthesis of Peptide 12842, the chemical structure of which is [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12844, the chemical structure of which is [(Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Ac-Ada-OH.

For the synthesis of Peptide 12846, the chemical structure of which is [(CH$_3$—(CH$_2$)$_{10}$—CO-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with (CH$_3$—(CH$_2$)$_{10}$—CO-Ada-OH.

For the synthesis of Peptide 12848, the chemical structure of which is [(DcaAda)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Dca-Ada-OH.

For the synthesis of Peptide 12850, the chemical structure of which is [PhF$_5$Ac$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12852, the chemical structure of which is [PhAc$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 12854, the chemical structure of which is [Dca$^0$-Tyr$^1$, D-Arg$^2$, Cpa$^6$, (Me-Ala)$^8$, Har$^9$, Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Dca-OH.

For the synthesis of Peptide 12860, the chemical structure of which is [(PhF$_5$Ac-Ada)$^0$-Tyr[1], D-Arg[2], Fpa5[6], (Me-Ala)[8], Har[9], Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-Ada-OH.

For the synthesis of Peptide 12862, the chemical structure of which is [(PhAc-Ada)$^0$-Tyr[1], D-Arg[2], Fpa5[6], (Me-Ala)[8], Har[9], Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-Ada-OH.

For the synthesis of Peptide 12864, the chemical structure of which is [(Ac-Ada)$^0$-Tyr[1], D-Arg[2], Fpa5[6], (Me-Ala)[8], Har[9], Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with Ac-Ada-OH.

For the synthesis of Peptide 12866, the chemical structure of which is [(CH$_3$—(CH$_2$)$_{10}$—CO-Ada)$^0$-Tyr[1], D-Arg[2], Fpa5[6], (Me-Ala)[8], Har[9], Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with (CH$_3$—(CH$_2$)$_{10}$—CO-Ada-OH.

For the synthesis of Peptide 12868, the chemical structure of which is [(Dca-Ada)$^0$-Tyr[1], D-Arg[2], Fpa5[6], (Me-Ala)[8], Har[9], Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with Dca-Ada-OH.

For the synthesis of Peptide 12870, the chemical structure of which is [PhF$_5$Ac$^0$-Tyr[1], D-Arg[2], Fpa5[6], (Me-Ala)[8], Har[9], Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhF$_5$Ac-OH.

For the synthesis of Peptide 12872, the chemical structure of which is [PhAc$^0$-Tyr[1], D-Arg[2], Fpa5[6], (Me-Ala)[8], Har[9], Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 12874, the chemical structure of which is [Dca$^0$-Tyr[1], D-Arg[2], Fpa5[6], (Me-Ala)[8], Har[9], Fpa5[10], His[11], Orn[12], His[15], Glu[17], His[20], Orn[21], Nle[27], D-Arg[28], Har[29], Ada[30]]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-(Me-Ala)-OH, Boc-Thr(Bzl)-OH, Boc-Fpa5-OH, Boc-Ile-OH, Boc-Ala-OH, Boc-Asp(OcHx)-OH, Boc-D-Arg(Tos)-OH, Boc-Tyr(2BrZ)-OH, followed by acylation with Dca-OH.

For the synthesis of Peptide 12920, the chemical structure of which is [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH, the following protected amino acids are coupled in the indicated order on the Ada-Merrifield resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Glu(OcHx)-OH, Boc-Gln-OH, Boc-His(Bom)-OH, Boc-Leu-OH, Boc-Val-OH, Boc-Orn(2ClZ)-OH, Boc-His(Bom)-OH, Boc-Fpa5-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Fpa5-OH, followed by acylation with PhAc-Ada-OH.

Example V

Aqueous Solution for Intramuscular Injection

| | |
|---|---|
| [PhAc$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$, Ada$^{30}$]hGH-RH(1-30)NH$_2$ (Peptide 12610) | 500.0 mg |
| Gelatin, nonantigenic | 5.0 mg |
| Water for injection q.s. | ad 100.0 mL |

The gelatin and GH-RH antagonist Peptide 12610 are dissolved in water for injection, and then the solution is sterile filtered.

Example VI

Long Acting Intramuscular Injectable Formulation

Sesame Oil Gel

| | |
|---|---|
| [(PhF$_5$Ac-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$ (Peptide 12692) | 10.0 mg |
| Aluminum monostearate, USP | 20.0 mg |
| Sesame oil q.s. | ad 1.0 mL |

The aluminum monostearate is combined with the sesame oil and heated to 125° C. with stirring until a clear yellow solution forms. This mixture is then autoclaved for sterility and allowed to cool. The GH-RH antagonist Peptide 12692 is then added aseptically with trituration. Particularly preferred antagonists are salts of low solubility, e.g., pamoate salts and the like. These exhibit long duration of activity.

Example VII

Long Acting Intramuscular (IM) Injectable-Biodegradable Polymer Microcapsules

Microcapsules are made from the following:
25/75 glycolide/lactide copolymer (0.5 intrinsic viscosity) 99%

| | |
|---|---|
| [PhAc$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH (Peptide 12852) | 1% |

25 mg of the above microcapsules are suspended in 1.0 mL of the following vehicle:

| | |
|---|---|
| Dextrose | 5.0% |
| CMC, sodium | 0.5% |
| Benzyl alcohol | 0.9% |
| Tween 80 | 0.1% |
| Water, purified q.s. | ad 100% |

Biological Activity in Endocrine and Oncological Assays

The peptides of the present invention were tested in assays in vitro and in vivo for their ability to inhibit the hGH-RH(1-29)NH$_2$ induces GH release. Binding affinities of the compounds to the tumoral GH-RH receptors were also measured. The antitumor activities of the peptides and their inhibitory effects on serum IGF-I and on the tumoral IGF, VEGF and FGF system were evaluated in various cancer models in vivo. Inhibitory effects on phosphorylated PI3K/AKT and MAPK (ERK1/2) were also measured.

Male nude mice were implanted s.c. with 3 mm3 pieces of PC-3 human hormone-independent prostate cancer tissue on both flanks. When tumors reached a volume of approximately 50 mm3, the mice were divided into 14 experimental groups with 8 to 10 animals in each group and received single daily injections for 28 as follows: 1. Control (vehicle solution); 2. P-12211 (2 µg/day s.c.); 3. P-12307 (2 µg/day s.c.); 4. P-12317 (2 µg/day s.c.); 5. P-12408 (2 µg/day s.c.); 6. P-12409 (2 µg/day s.c.); 7. P-12457 (2 µg/day s.c.); 8. P-12473 (2 µg/day s.c.); 9. P-12479 (2 µg/day s.c.); 10. P-12600 (2 µg/day s.c.); 11. P-12601 (2 µg/day s.c.); 12. P-12602 (2 µg/day s.c.); 13. P-12603 (2 µg/day s.c.); and 14. P-12610 (2 µg/day s.c.).

All peptides of the present application, tested at the dose of 2 µg/day, potently inhibited the growth of PC-3 tumors. The inhibitory effect of P-12473, P-12479, P-12600, P-12601, P-12602, and P-12610 were statistically significant ($p<0.001$). The results are shown in Table I and Graphs I and II.

Effect of Treatment with GH-RH Antagonists on PC-3 Human Prostate Cancer Xenografts in Nude Mice

| Group | Tumor Growth after 4 weeks (%) | Tumor growth inhibition after 4 weeks (%) | Significance versus control |
|---|---|---|---|
| Control | 2137.62 | — | — |
| P-12211 (2 ug/day) | 1491.95 | 30.21 | N.S. |
| P-12307 (2 ug/day) | 878.85 | 58.89 | N.S. |
| P-12317 (2 ug/day) | 1236.06 | 42.18 | N.S. |
| P-12408 (2 ug/day) | 1128.06 | 47.23 | N.S. |

-continued

| Group | Tumor Growth after 4 weeks (%) | Tumor growth inhibition after 4 weeks (%) | Significance versus control |
|---|---|---|---|
| P-12409 (2 ug/day) | 1671.55 | 21.80 | N.S. |
| P-12457 (2 ug/day) | 1117.90 | 47.70 | N.S. |
| P-12473 (2 ug/day) | 748.61 | 64.98 | $p < 0.001$ |
| P-12479 (2 ug/day) | 790.29 | 63.03 | $p < 0.001$ |
| P-12600 (2 ug/day) | 735.97 | 65.57 | $p < 0.001$ |
| P-12601 (2 ug/day) | 513.22 | 75.99 | $p < 0.001$ |
| P-12602 (2 ug/day) | 728.60 | 65.92 | $p < 0.001$ |
| P-12603 (2 ug/day) | 1271.91 | 40.50 | N.S. |
| P-12610 (2 ug/day) | 474.98 | 77.78 | $p < 0.001$ |

N.S., not significant

We claim:

1. A peptide selected from the group having the formulae:
[$R_1$-$A^0$, $A^1$, $A^2$, $A^6$, $A^8$, $A^9$, $A^{10}$, $A^{11}$, $A^{12}$, $A^{13}$, $A^{15}$, $A^{17}$, $A^{19}$, $A^{20}$, $A^{21}$, $A^{22}$, $A^{23}$, $A^{27}$, $A^{28}$, $A^{29}$, $A^{30}$]hGH-RH(1-30)-$R_2$
wherein
  $R_1$ PhAc, PhF$_5$Ac, CH$_3$(CH$_2$)$_{10}$CO, Ac, Tfa or Dca,
  $A^0$ is Dca, PhAc, PhF$_5$Ac, (Dca-Ada), (CH$_3$—(CH$_2$)$_{10}$—CO-Ada), (Ac-Ada), (PhAc-Ada), or (PhF$_5$Ac-Ada) ω-Ada, Amc, or is absent,
  $A^1$ is L-Fpa, D-Fpa, Tyr, D-Tyr, His, D-His or Fpa5,
  $A^2$ is D-Arg, D-Har, D-Cit, or D-Amp,
  $A^6$ is Fpa, Fpa5, or Cpa,
  $A^8$ is Asn, D-Asn, Cit, D-Cit, Gln, D-Gln, Ser, D-Ser, Thr, D-Thr, Ala, D-Ala, N-Me-Ala, N-Me-D-Ala, Abu, D-Abu, or Aib,
  $A^9$ is Har, D-Har, Arg, D-Arg, Fpa, D-Fpa, His, D-His, Amp, D-Amp, Gup, or D-Gup,
  $A^{10}$ is di- or poly-fluorinated (on the aromatic ring) Phe, Fpa2, Fpa3, Fpa4, or Fpa5,
  $A^{11}$ is His, D-His, Arg, D-Arg, Cit, D-Cit, Har, D-Har, Amp, D-Amp, Gup, or D-Gup,
  $A^{12}$ is Lys, D-Lys, Lys(Me)$_2$, Lys(iPr), Orn, D-Orn, Har, D-Har, Cit, D-Cit, Nle, D-Nle, Ala, or D-Ala,
  $A^{13}$ is Fpa, or Val,
  $A^{15}$ is Fpa, Gly, Ala, Abu, Aib, Nle, Gln, Cit, or His,
  $A^{17}$ is Leu or Glu,
  $A^{19}$ is Ala or Abu,
  $A^{20}$ is His, D-His, Arg, D-Arg, Har, D-Har, Amp, D-Amp, Cit, or D-Cit,
  $A^{21}$ is Lys, D-Lys, Lys(Me)$_2$, Lys(iPr), Orn, D-Orn, Har, D-Har, Cit, or D-Cit,
  $A^{22}$ is Fpa, Leu, Tyr, Ala, or Aib,
  $A^{23}$ is Fpa, Leu, Tyr, Ala, or Aib,
  $A^{27}$ is Nle, Met, Leu, Ala, Abu, α-Apa, α-Ahea, or α-Aoc,
  $A^{28}$ is Arg, D-Arg, Har, D-Har, Ser, Asn, Asp, Ala, Abu, or Cit,
  $A^{29}$ is Arg, D-Arg, Har, or Agm,
  $A^{30}$ is, Arg, Ada, D-Arg, Har, Agm, or is absent,
  $R_2$ is —NH$_2$, or —OH,
  provided that when $A^{17}$ is Leu and $A^{30}$ is Ada, then $A^{15}$ is other than Abu, also
  provided that if $A^{29}$ is Agm then $A^{30}$ and $R_2$ are absent, and if $A^{30}$ is Agm then $R_2$ is absent,
  and pharmaceutically acceptable salts thereof.

2. The peptide of claim 1 wherein one or more of the substituents $A^1$, $A^6$, and $A^{10}$ are Fpa3, Fpa4, Fpa5 or 3,4,5-tri-fluoro-Phe, and pharmaceutically acceptable salts thereof.

3. The peptide of claim 2 wherein one or more of the substituents $A^1$, $A^6$, and $A^{10}$ are either Fpa4 or Fpa5.

4. The peptide of claim 2 wherein, the substituent in at least one member of the group consisting of $A^1$, $A^6$, or $A^{10}$, is Fpa4 or Fpa5.

5. The peptide of claim 2 wherein:
  $R_1$ is Ac, (Ac-Ada), PhAc and PhF$_5$Ac,
  $A^1$ is Tyr or Fpa5,
  $A^6$ is Fpa5,
  $A^8$ is (Me-Ala),
  $A^{10}$ is Fpa5,
  $A^{15}$ is His,
  $A^{17}$ is Glu,
  $A^{30}$ is Ada or Agm,
  $R_2$ is —NH$_2$, or —OH.

6. The peptide of claim 1 selected from the group having the formulae:

P-12610 [PhAc$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$, Ada$^{30}$]hGH-RH(1-30)NH$_2$

P-12640 [PhAc$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12642 [PhAc$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12644 [PhAc$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12646 [(PhAc-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$

P-12650 [(PhF$_5$Ac)$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$,]hGH-RH(1-29)NH$_2$

P-12652 [(PhF$_5$Ac)$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12654 [(PhF$_5$Ac)$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12656 [(PhF$_5$Ac)$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12660 [PhAc$^0$-Tyr$^1$, D-Arg$^2$, Cpa$^6$, Ala$^8$, Har$^9$, Fpa5$^{10}$, His$^{11}$, Orn$^{12}$, His$^{15}$, His$^{20}$, Orn$^{21}$, Nle$^{27}$, D-Arg$^{28}$, Har$^{29}$, Ada$^{30}$]hGH-RH(1-30)NH$_2$

P-12662 [PhAc$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12664 [(PhF$_5$Ac)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12666 [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12670 [PhAc$^0$-Tyr$^1$, D-Arg$^2$, Fpa5$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12672 [(PhF$_5$Ac)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12674 [(PhF$_5$Ac)$^0$-Tyr$^1$,, D-Arg$^2$, Fpa5$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12680 [(Ac-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$

P-12682 [(Ac-Ada)$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$

P-12684 [(Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$,]hGH-RH(1-29)NH$_2$

P-12690 [(PhAc-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$

P-12692 [(PhF$_5$Ac-Ada)$^0$-Tyr$^1$, D-Arg$^2$, Cpa$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$

P-12694 [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$

P-12696 [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, His$^{20}$, Orn$^{21}$, Nle$^{27}$, D-Arg$^{28}$, Har$^{29}$]hGH-RH(1-29)NH$_2$

P-12698 [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$

P-12710 [(PhAc-Ada)$^0$-Tyr$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$

P-12712 [(PhAc-Ada)$^0$-Tyr$^1$, D-Arg$^2$, Cpa$^6$, Ala$^8$, Har$^9$, Fpa5$^{10}$, His$^{11}$, Leu$^{13}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$

P-12714 [PhF$_5$Ac$^0$-Tyr$^1$, D-Arg$^2$, Cpa$^6$, Ala$^8$, Har$^9$, Fpa5$^{10}$, His$^{11}$, Leu$^{13}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$

P-12716 [(PhF$_5$Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$

P-12720 [(CH$_3$—(CH$_2$)$_{10}$—CO-Ada)$^0$-Tyr$^1$, D-Arg$^2$, Cpa$^6$, (Me-Ala)$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$

P-12730 [(PhAc-Ada)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$

P-12740 [(PhAc-Ada)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12750 [(PhAc-Ada)$^0$-Tyr$^1$, D-Arg$^2$, Fpa5$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$

P-12760 [(CH$_3$—(CH$_2$)$_{10}$—CO-Ada)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$

P-12770 [(Ac-Ada)$^0$-Tyr$^1$, D-Arg$^2$, Fpa5$^6$, Ala$^8$, Har$^9$, Fpa5$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$

P-12780 [(PhF$_5$Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)NH$_2$

P-12800 [(PhF$_5$Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30)

P-12802 [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30)

P-12804 [(Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30)

-continued

| | |
|---|---|
| P-12806 | [(CH$_3$—(CH$_2$)$_{10}$—CO-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30) |
| P-12808 | [(Dca-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30) |
| P-12810 | [(PhF$_5$Ac-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30) |
| P-12812 | [(PhAc-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30) |
| P-12814 | [(Ac-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30) |
| P-12816 | [(CH$_3$—(CH$_2$)$_{10}$—CO-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30)NH$_2$ |
| P-12818 | [(Dca-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-30) |
| P-12840 | [(PhF$_5$Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12842 | [(PhAc-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12844 | [(Ac-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12846 | [(CH$_3$—(CH$_2$)$_{10}$—CO-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{99}$, Ada$^{30}$]hGH-RH(1-30)OH |
| P-12848 | [(Dca-Ada)$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12850 | [PhF$_5$Ac-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12852 | [PhAc$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12854 | [Dca$^0$-Tyr$^1$, D-Arg$^2$, Cpa$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12860 | [(PhF$_5$Ac-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12862 | [(PhAc-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12864 | [(Ac-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12866 | [(CH$_3$—(CH$_2$)$_{10}$—CO-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12868 | [(Dca-Ada)$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12870 | [PhF$_5$Ac$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12872 | [PhAc$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12874 | [Dca$^0$-Tyr$^1$, D-Arg$^2$, Fpa5$^6$, (Me-Ala)$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-30)OH |
| P-12880 | [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$]hGH-RH(1-29)NH$_2$ |
| P-12890 | [PhAc$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-29)NH$_2$ |
| P-12900 | [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Agm$^{30}$]hGH-RH(1-29)NH$_2$ |
| P-12920 | [(PhAc-Ada)$^0$-Fpa5$^1$, D-Arg$^2$, Cpa$^6$, Ala$^8$, Har$^9$, Fpa5$^{10}$, His$^{11}$, Orn$^{12}$, His$^{15}$, Glu$^{17}$, His$^{20}$, Orn$^{21}$, Nle$^{27}$, D-Arg$^{28}$, Har$^{29}$, Ada$^{30}$]hGH-RH(1-29)OH. |

7. A method of suppressing levels of GH in a patient in need of same by administering to said patient a suppressively effective amount of a compound of claim 1.

8. A method of suppressing levels of IGF-I in a patient in need of same by administering to said patient a suppressively effective amount of a compound of claim 1.

9. A method of suppressing serum IGF-I levels in a patient having a cancer carrying receptors for IGF-I by administering to said patient a suppressively effective amount of a compound of claim 1.

10. A method of decreasing the occurrence of restenosis of blood vessels in a patient by administering to said patient in need of same an effective amount of a compound of claim 1 sufficient to provide such decrease.

11. The method of claim 10 wherein the restenosis is caused by the prior insertion of a therapeutically effective device into an appropriate location in the patient.

12. The method of claim 11 wherein the device is a stent.

13. The method of claim 12 wherein the stent is a synthetic stent.

14. The method of claim 11 wherein the stent is inserted as part of the process of percutaneous coronary angioplasty.

15. The method of claim 10 wherein restenosis occurs during dialysis of the patient.

16. The method of claim 15 wherein the compound is administered in the dialysis fluid.

17. The method of claim 11 wherein the compound is coated onto the surface of the device.

18. The method of claim 11 wherein the compound is incorporated into the device.

19. A pharmacologically administrable composition consisting essentially of a compound of claim 1 and a pharmacologically acceptable carrier.

* * * * *